(12) United States Patent
Djupesland

(10) Patent No.: US 9,205,208 B2
(45) Date of Patent: Dec. 8, 2015

(54) NASAL DEVICES

(75) Inventor: Per Gisle Djupesland, Oslo (NO)

(73) Assignee: OptiNose AS, Oslo (NO)

(*) Notice: Subject to any disclaimer, the term of this patent is extended or adjusted under 35 U.S.C. 154(b) by 0 days.

(21) Appl. No.: 13/180,492

(22) Filed: Jul. 11, 2011

(65) Prior Publication Data

US 2012/0006323 A1    Jan. 12, 2012

Related U.S. Application Data

(63) Continuation of application No. 10/480,582, filed on Sep. 23, 2004, now Pat. No. 7,975,690.

(30) Foreign Application Priority Data

Jun. 12, 2001 (GB) .................... 0114272.8
Jun. 12, 2002 (WO) ............. PCT/IB02/03034

(51) Int. Cl.
*A61M 15/00* (2006.01)
*A61M 15/08* (2006.01)

(52) U.S. Cl.
CPC ....... *A61M 15/0091* (2013.01); *A61M 15/0098* (2014.02); *A61M 15/08* (2013.01); *A61M 2202/064* (2013.01); *A61M 2210/0618* (2013.01); *A61M 2210/0625* (2013.01)

(58) Field of Classification Search
CPC .......... A61M 11/007; A61M 15/0091; A61M 15/0098; A61M 15/08; A61M 2202/064; A61M 2210/0625; A61M 2210/0618
USPC ........ 128/DIG. 26, 911, 912, 207.15, 207.16, 128/207.18, 207.17, 204.11, 204.12, 128/204.18, 200.24, 206.11, 207.11, 128/200.26, 201.22, 203.21, 128/200.13–200.23, 203.12, 203.15, 128/203.16, 203.18, 203.22, 203.23, 128/204.14, 205.18; 604/94
See application file for complete search history.

(56) References Cited

U.S. PATENT DOCUMENTS

| | | | | | |
|---|---|---|---|---|---|
| 746,749 | A | * | 12/1903 | Seidel | 128/203.18 |
| 1,873,160 | A | * | 8/1932 | Sturtevant | 128/206.11 |
| 2,470,297 | A | * | 5/1949 | Fields | 128/203.15 |
| 3,730,179 | A | * | 5/1973 | Williams | 128/204.18 |
| 4,263,908 | A | * | 4/1981 | Mizerak | 128/205.25 |
| 4,705,034 | A | * | 11/1987 | Perkins | 128/204.21 |
| 5,201,308 | A | * | 4/1993 | Newhouse | 128/203.15 |
| 5,269,296 | A | * | 12/1993 | Landis | 128/207.18 |

(Continued)

FOREIGN PATENT DOCUMENTS

| | | |
|---|---|---|
| EP | 0 658 356 | 6/1995 |
| EP | 0 768 094 | 4/1997 |

(Continued)

OTHER PUBLICATIONS

U.S. Appl. No. 12/871,443, filed Aug. 30, 2010, Djupesland.

(Continued)

*Primary Examiner* — Nicholas Woodall
*Assistant Examiner* — Raymond E Harris
(74) *Attorney, Agent, or Firm* — Finnegan, Henderson, Farabow, Garrett and Dunner, LLP

(57) ABSTRACT

A nasal delivery device for and a method of delivering a substance, in particular one of a liquid, as a suspension or solution, or a powder containing a medicament, especially systemic or topical pharmaceuticals, or a vaccine to the nasal airway of a subject.

14 Claims, 36 Drawing Sheets

(56) References Cited

U.S. PATENT DOCUMENTS

| | | | |
|---|---|---|---|
| 5,513,634 A * | 5/1996 | Jackson | 128/207.18 |
| 5,560,354 A * | 10/1996 | Berthon-Jones et al. | 128/205.25 |
| 5,596,983 A * | 1/1997 | Zander et al. | 128/204.18 |
| 5,649,530 A * | 7/1997 | Ballini | 128/200.14 |
| 5,666,948 A | 9/1997 | Matson | |
| 5,687,715 A | 11/1997 | Landis et al. | |
| 5,687,746 A | 11/1997 | Rose et al. | |
| 5,823,178 A * | 10/1998 | Lloyd et al. | 128/200.14 |
| 6,076,520 A | 6/2000 | Cooper | |
| 6,216,966 B1 * | 4/2001 | Prendergast et al. | 239/690 |
| 6,269,810 B1 | 8/2001 | Brooker et al. | |
| 6,379,312 B2 * | 4/2002 | O'Toole | 600/529 |
| 6,561,193 B1 | 5/2003 | Noble | |
| 6,715,485 B1 * | 4/2004 | Djupesland | 128/203.15 |
| 7,347,201 B2 | 3/2008 | Djupesland | |
| 7,377,901 B2 | 5/2008 | Djupesland et al. | |
| 7,481,218 B2 * | 1/2009 | Djupesland | 128/206.11 |
| 7,543,581 B2 * | 6/2009 | Djupesland | 128/200.14 |
| 7,740,014 B2 | 6/2010 | Djupesland | |
| 7,784,460 B2 | 8/2010 | Djupesland et al. | |
| 7,841,337 B2 | 11/2010 | Djupesland | |
| 7,854,227 B2 | 12/2010 | Djupesland | |
| 7,934,503 B2 | 5/2011 | Djupesland | |
| 7,975,690 B2 | 7/2011 | Djupesland | |
| 2004/0112379 A1 | 6/2004 | Djupesland | |
| 2004/0182388 A1 | 9/2004 | Djupesland | |
| 2005/0235992 A1 | 10/2005 | Djupesland | |
| 2006/0219240 A1 | 10/2006 | Djupesland | |
| 2006/0219241 A1 | 10/2006 | Djupesland | |
| 2006/0225732 A1 | 10/2006 | Djupesland | |
| 2006/0231094 A1 | 10/2006 | Djupesland | |
| 2007/0039614 A1 | 2/2007 | Djupesland | |
| 2007/0125371 A1 | 6/2007 | Djupesland | |
| 2008/0161771 A1 | 7/2008 | Djupesland | |
| 2008/0163874 A1 | 7/2008 | Djupesland | |
| 2008/0221471 A1 | 9/2008 | Djupesland | |
| 2008/0223363 A1 | 9/2008 | Djupesland | |
| 2008/0289629 A1 | 11/2008 | Djupesland | |
| 2009/0101146 A1 | 4/2009 | Djupesland | |
| 2009/0293873 A1 | 12/2009 | Djupesland | |
| 2009/0304802 A1 | 12/2009 | Djupesland | |
| 2009/0314293 A1 | 12/2009 | Djupesland | |
| 2009/0320832 A1 | 12/2009 | Djupestand | |
| 2010/0035805 A1 | 2/2010 | Hafner | |
| 2010/0051022 A1 | 3/2010 | Djupesland | |
| 2010/0057047 A1 | 3/2010 | Djupesland | |
| 2010/0242959 A1 | 9/2010 | Djupesland | |
| 2010/0282246 A1 | 11/2010 | Djupesland et al. | |
| 2010/0288275 A1 | 11/2010 | Djupesland et al. | |
| 2010/0300439 A1 | 12/2010 | Djupesland et al. | |
| 2011/0023869 A1 | 2/2011 | Djupesland | |
| 2011/0053827 A1 | 3/2011 | Hafner | |
| 2011/0088690 A1 | 4/2011 | Djupesland | |
| 2011/0088691 A1 | 4/2011 | Djupesland | |
| 2011/0114087 A1 | 5/2011 | Djupesland | |
| 2011/0126830 A1 | 6/2011 | Djupesland | |

FOREIGN PATENT DOCUMENTS

| | | |
|---|---|---|
| JP | 9-140797 | 11/1995 |
| JP | 10-033678 | 2/1998 |
| WO | 94/17753 | 8/1994 |
| WO | 97/32539 | 9/1997 |
| WO | 98/53869 | 12/1998 |
| WO | 00/44432 | 8/2000 |
| WO | 00/51672 | 9/2000 |
| WO | WO 0051672 A1 * | 9/2000 |

OTHER PUBLICATIONS

U.S. Appl. No. 12/955,546, filed Nov. 29, 2010, Djupesland.
U.S. Appl. No. 12/973,317, filed Dec. 20, 2010, Djupesland.
U.S. Appl. No. 13/063,963, filed Mar. 15, 2011, Djupesland.
U.S. Appl. No. 13/099,183, filed May 2, 2011, Djupesland.
U.S. Appl. No. 13/180,492, filed Jul. 11, 2011, Djupesland.

* cited by examiner

NASAL DEVICES

CROSS-REFERENCE TO RELATED APPLICATIONS

This application is a Continuation of U.S. Ser. No. 10/480,582 filed on Sep. 23, 2004 and issued as U.S. Pat. No. 7,975,690, which is a National Phase Application of International Application No. PCT/IB02/03034 filed Jun. 12, 2002, which claims benefit of priority to British Application No. GB 0114272.8 filed Jun. 12, 2001, all of which are owned by the assignee of the instant application and the disclosures of which are incorporated herein by reference in their entireties.

BACKGROUND OF THE INVENTION

The present invention relates to a nasal delivery device for and a method of delivering a substance, in particular one of a liquid, as a suspension or solution, or a powder containing a medicament, especially systemic or topical pharmaceuticals, or a vaccine to the nasal airway of a subject.

Referring to FIG. 1, the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and antimicrobial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitionin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as *helicobacter pylori* infections which cause gastric ulcers.

WO-A-00/51672 discloses a delivery device for delivering a substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

It is an aim of the present invention to provide improved nasal delivery devices and nasal delivery methods for providing for the improved delivery of a substance to a nasal cavity of subject.

BRIEF SUMMARY OF THE INVENTION

In one aspect the present invention provides a nasal delivery device for delivering substance to a nasal airway of a subject, comprising: a nosepiece for fitting to a nostril of a subject, the nosepiece including a nozzle through which substance is in use delivered to the nasal airway, and at least one inflatable cuff member which is configured to be inflated subsequent to exhalation by the subject; and a delivery unit for delivering substance through the nozzle of the nosepiece.

In another aspect the present invention provides a nasal delivery device for delivering substance to a nasal cavity of a subject, comprising: a nosepiece including a nozzle through which substance is in use delivered to the nasal cavity, and at least one inflatable cuff member which is configured such as, when inflated, to provide a fluid-tight seal between the nosepiece and an inner wall of the nasal cavity of the subject; and a delivery unit for delivering substance through the nozzle of the nosepiece.

In a further aspect the present invention provides a nasal delivery device for delivering substance to a nasal airway of a subject, comprising: a nosepiece for fitting to a nostril of a subject, the nosepiece including a nozzle through which substance is in use delivered to the nasal airway, and at least one cuff member which is configured such as, when fitted in a nasal cavity of the subject, to engage an inner wall of the nasal cavity of the subject and direct at least a distal end of the nozzle towards a site in the nasal airway of the subject; and a delivery unit for delivering substance through the nozzle of the nosepiece.

In yet another aspect the present invention provides a nasal delivery device for delivering substance to a nasal airway of a subject, comprising: a nosepiece for fitting to a nostril of a subject, the nosepiece including a nozzle through which substance is in use delivered to the nasal airway, and at least one cuff member, at least one of the at least one cuff member including at least one lobe which, when the at least one of the at least one cuff member is fitted in the nasal cavity of the subject, extends into a region of the nasal cavity of the subject such as to at least partially obstruct the same and prevent flow thereinto; and a delivery unit for delivering substance through the nozzle of the nosepiece.

In a yet further aspect the present invention provides a nasal delivery device for delivering substance to a nasal airway of a subject, comprising: a nosepiece for fitting to a nasal cavity of a subject, the nosepiece including a first delivery outlet through which substance is in use delivered to the nasal airway of the subject, and at least one second delivery outlet through which at least one gas flow, separate to an exhalation breath of the subject, is in use delivered to the nasal airway of the subject; a delivery unit for delivering substance through the first delivery outlet of the nosepiece; and a gas supply unit for supplying a flow of gas through the at least one second delivery outlet of the nosepiece.

In yet another further aspect the present invention provides a method of delivering substance to a nasal airway of a subject, comprising: fitting a nosepiece to a nasal cavity of a subject, the nosepiece including a nozzle through which substance is delivered to the nasal airway, and at least one inflatable cuff member; inflating the at least one cuff member subsequent to exhalation by the subject; and delivering substance through the nozzle of the nosepiece.

In a still further aspect the present invention provides a method of delivering substance to a nasal cavity of a subject, comprising the steps of: fitting a nosepiece to a nasal cavity of a subject, the nosepiece including a nozzle through which substance is delivered to the nasal cavity, and at least one inflatable cuff member which is configured such as, when inflated, to provide a fluid-tight seal between the nosepiece and an inner wall of the nasal cavity of the subject; and delivering substance through the nozzle of the nosepiece.

In still yet another further aspect the present invention provides a method of delivering substance to a nasal airway of a subject, comprising the steps of: fitting a nosepiece to a nasal cavity of a subject, the nosepiece including a nozzle through which substance is delivered to the nasal airway, and at least one cuff member which is configured such as, when fitted in the nasal cavity of the subject, to engage an inner wall of the nasal cavity of the subject and direct at least a distal end of the nozzle towards a site in the nasal airway of the subject; and delivering substance through the nozzle of the nosepiece.

In a still yet further aspect the present invention provides a method of delivering substance to a nasal airway of a subject, comprising the steps of: fitting a nosepiece to a nasal cavity of a subject, the nosepiece including a nozzle through which substance is delivered to the nasal airway, and at least one cuff member, at least one of the at least one cuff member including at least one lobe which, when the at least one of the at least one cuff member is fitted in the nasal cavity of the subject, extends into a region of the nasal cavity of the subject such as to at least partially obstruct the same and prevent flow thereinto; and delivering substance through the nozzle of the nosepiece.

In a still yet another further aspect the present invention provides a method of delivering substance to a nasal airway of a subject, comprising the step of: delivering substance through a first delivery outlet and at least one gas flow, separate to an exhalation breath of a subject, through at least one second delivery outlet into the nasal airway of the subject.

BRIEF DESCRIPTION OF THE SEVERAL VIEWS OF THE DRAWINGS

Preferred embodiments of the present invention will now be described hereinbelow by way of example only with reference to the accompanying drawings, in which.

DETAILED DESCRIPTION OF THE INVENTION

Figure 1:
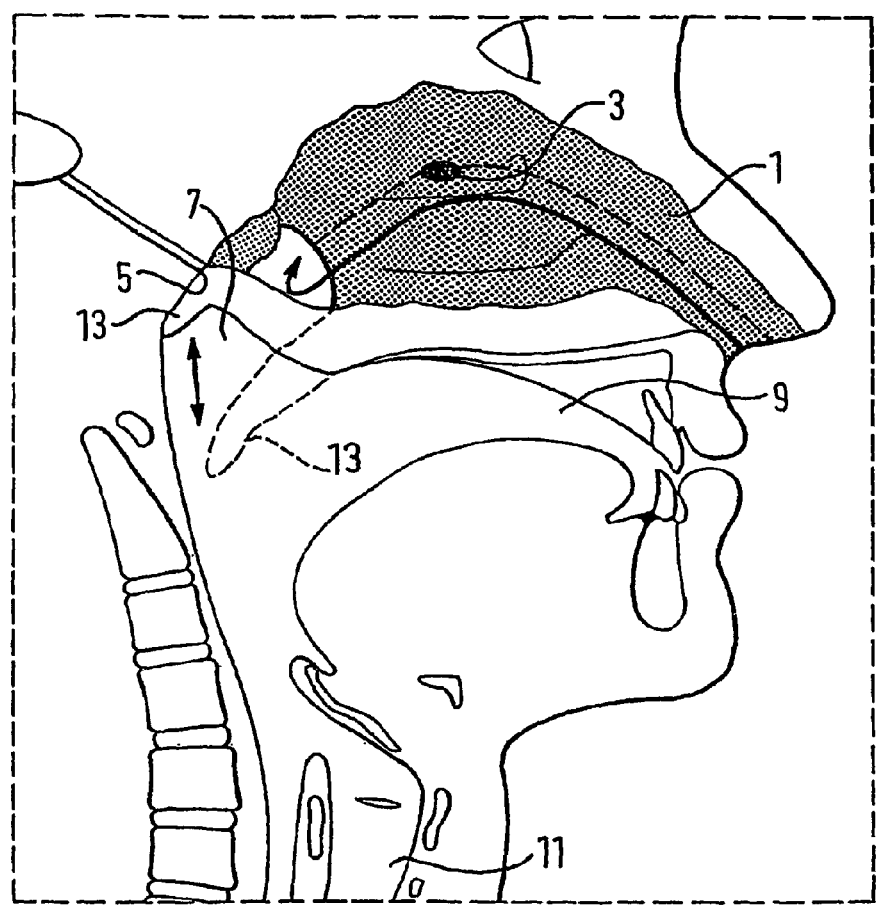
FIG. 1 schematically illustrates the anatomy of the upper respiratory tract of a human subject.
Figure 2:
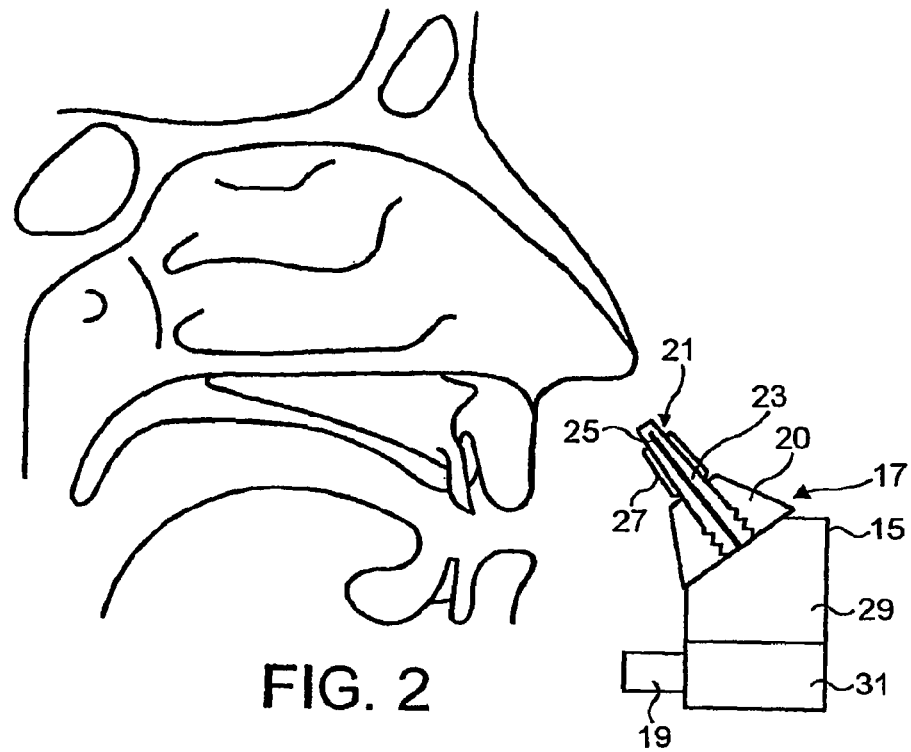
FIG. 2 schematically illustrates a nasal delivery device in accordance with a first embodiment of the present invention.

FIGS. 2 to 5 illustrate an exhalation breath-actuated nasal delivery device in accordance with a first embodiment of the present invention.

The delivery device comprises a housing 15, a nosepiece 17 for fitting in a nasal cavity of a subject, and a mouthpiece 19 through which the subject exhales to actuate the delivery device.

The nosepiece 17 comprises a guide member 20, in this embodiment a frusto-conical element, for guiding the nosepiece 17 into a nasal cavity of the subject, and an outlet unit 21 for delivering substance into the nasal airway of the subject. In this embodiment the nosepiece 17 is a replaceable unit.

In this embodiment the outlet unit 21 comprises a delivery channel 23 which is in fluid communication with the mouthpiece 19 such that an air flow is delivered into and through the nasal airway of the subject on exhalation by the subject through the mouthpiece 19, and a nozzle 25 for delivering substance to the nasal airway of the subject. In this embodiment the nozzle 25 is disposed in the delivery channel 23 co-axially with the same. In this embodiment the nozzle 25 is configured to provide an aerosol spray. In an alternative embodiment, for the delivery of a liquid, the nozzle 25 could be configured to deliver a liquid jet as a column of liquid.

In this embodiment the outlet unit 21 is movably coupled to the housing 15, here as provided by a flexible coupling, such as to allow for the positioning of the outlet unit 21 in the nasal cavity of the subject, as will be described in more detail hereinbelow.

In an alternative embodiment the outlet unit 21 could be fixed to the housing 15, and the mouthpiece 19 instead movably coupled to the housing 15, here as provided by a flexible coupling, such as to allow for the positioning of the outlet unit 21 in the nasal cavity of the subject.

In this embodiment at least the tip of the delivery channel 23 comprises a tubular section of a flexible, preferably resilient, material. In a preferred embodiment the material is a semi-soft plastics material, such as silicone rubber.

In this embodiment at least the tip of the delivery channel 23 has a tapering section which narrows to the distal end thereof. The delivery channel 23, in having a narrowing taper, acts, on insertion, to expand the narrow nasal valve of the nasal cavity of the subject. In a preferred embodiment the delivery channel 23 has an elliptical section, preferably an oval section.

In a preferred embodiment the distal end of the outlet unit 21 is configured to extend at least about 2 cm, preferably at least about 3 cm, and more preferably from about 2 cm to about 3 cm, into the nasal cavity of the subject.

The nosepiece 17 further comprises at least one expandable cuff member 27 for expansion in the nasal cavity of the subject. In this embodiment the at least one cuff member 27 comprises an inflatable member.

In this embodiment the at least one cuff member 27 is in fluid communication with the delivery channel 23, whereby the air flow generated by the subject on exhalation through the mouthpiece 19 acts to inflate the at least one cuff member 27. In an alternative embodiment the delivery device could include a separate pump unit for inflating the at least one cuff member 27 subsequent to fitting of the nosepiece 17, and in a preferred embodiment subsequent to, preferably in response to, exhalation through the mouthpiece 19.

In this embodiment the at least one cuff member 27 is an inflatable member which is inflated on exhalation by the subject. In an alternative embodiment the at least one cuff member 27 could be inflated on the nosepiece 17 being located in the correct position.

In this embodiment the at least one cuff member 27 comprises a flexible balloon element which is inflated by the generation of a pressure in the delivery channel 23, with the at least one cuff member 27 deflating on the release of pressure from the delivery channel 23. In the alternative embodiment, where the at least one cuff member 27 is inflated by a separate pump unit, the at least one cuff member 27 could equally be deflated by the evacuation of gas therefrom using the same pump unit.

In one embodiment the at least one cuff member 27 could comprise a resilient balloon element which is inflated by the generation of a pressure in the delivery channel 23, with the at least one cuff member 27 returning to the original, deflated configuration on the release of pressure from the delivery channel 23.

In another embodiment the at least one cuff member 27 could comprise an inflatable sponge element, in one embodiment a foam element having an encapsulating sealing layer, which can be compressed, in this embodiment by evacuation, to adopt a compact configuration to allow for insertion into a nasal cavity of the subject and inflated, in this embodiment by breaking the vacuum, to allow for the introduction of a gas into the porous structure of the sponge element. In one embodiment such a cuff member 27 could be in selective fluid communication with the atmosphere. In another embodiment such a cuff member 27 could be in selective fluid communication with the delivery channel 23, whereby the pressure developed in the delivery channel 23 would assist in the inflation of the cuff member 27. In the alternative embodiment which includes a separate pump unit, the pump unit could be employed to assist in inflating such a cuff member 27 and in deflating the cuff member 27 by the evacuation of gas therefrom. In one embodiment the inflation could be triggered on exhalation by the subject. In another embodiment the inflation could be triggered on the nosepiece 17 being located in the correct position in the nasal cavity of the subject.

The at least one cuff member 27 is disposed to an outer surface of the outlet unit 21 such as, on expansion, to engage the inner wall of the nasal cavity of the subject. The at least one cuff member 27, in being expandable, provides for the expansion of the narrow nasal valve of the nasal cavity of the subject, the sealing of the nosepiece 17 in the nasal cavity of the subject, and the positioning, in particular the direction, of the outlet unit 21 in the nasal cavity of the subject.

In this embodiment the at least one cuff member 27 comprises a single annular cuff member 27 which is located about the outlet unit 21 such as to provide a seal between the delivery channel 23 and the inner wall of the nasal cavity of the subject when inflated.

In an alternative embodiment the at least one cuff member 27 could comprise a plurality of cuff members 27 which together provide a seal between the delivery channel 23 and the inner wall of the nasal cavity of the subject when inflated.

The delivery device further comprises a substance supply unit 29 for delivering metered doses of a substance, in this embodiment an aerosol canister for delivering metered volumes of a propellant, preferably a hydrofluoroalkane (HFA) propellant or the like, containing medicament, either as a suspension or solution, which is fluidly connected to the nozzle 25 to deliver substance from the nosepiece 17, in this embodiment as an aerosol spray.

In this embodiment the substance supply unit 29 is a multi-dose unit for delivering a plurality of metered doses of substance. In another embodiment the substance supply unit 29 could be a single-dose unit for delivering a single metered dose of substance.

The substance supply unit 29 is pre-primeable, in this embodiment by loading a resilient element, and includes a breath-actuated release mechanism 31 which, when triggered, releases the resilient element and actuates the substance supply unit 29 to deliver a metered dose of a substance through the nozzle 25.

In this embodiment the trigger mechanism 31 is configured to cause actuation of the substance supply unit 29 on generation of a predetermined flow rate through the delivery channel 23.

In another embodiment the trigger mechanism 31 could be configured to cause actuation of the substance supply unit 29 on generation of a predetermined pressure within the delivery channel 23.

In a further embodiment the trigger mechanism 31 could be configured to cause actuation of the substance supply unit 29 on generation of either one of a predetermined flow rate through the delivery channel 23 or a predetermined pressure within the delivery channel 23.

In an alternative embodiment the substance supply unit 29 could comprise a mechanical delivery pump, in particular a liquid delivery pump or a powder delivery pump, which delivers metered doses of a substance on actuation thereof.

In another alternative embodiment the substance supply unit 29 could comprise a dry powder delivery unit which delivers metered doses of a substance, as a dry powder, on actuation thereof.

In yet another alternative embodiment the substance supply unit 29 could comprise a nebulizer which delivers metered doses of a substance, as an aerosol spray, on actuation thereof.

Operation of the delivery device will now be described hereinbelow with reference to FIGS. 3 to 5 of the accompanying drawings.

Figure 3:
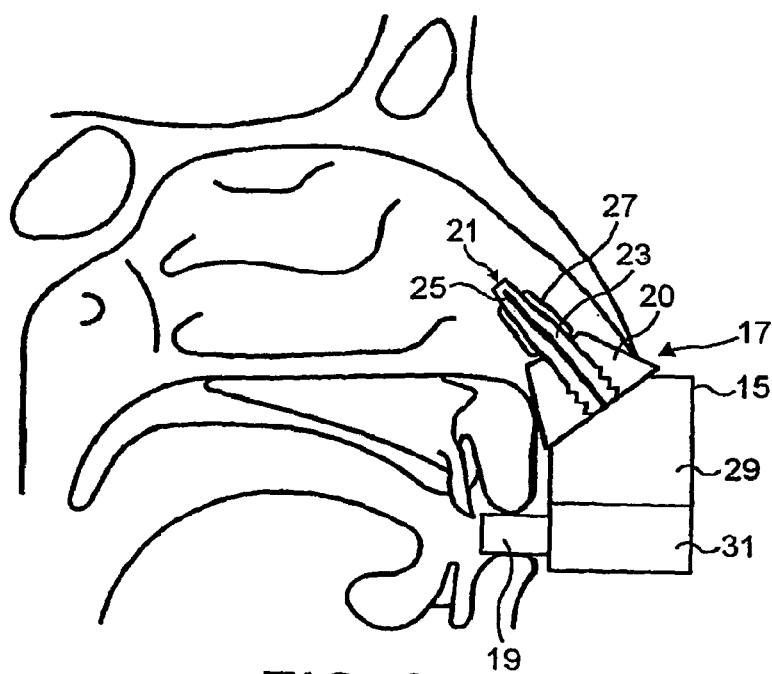
FIG. 3 schematically illustrates the delivery device of FIG. 2 inserted in a nasal cavity of a subject for operation.
Figure 4:
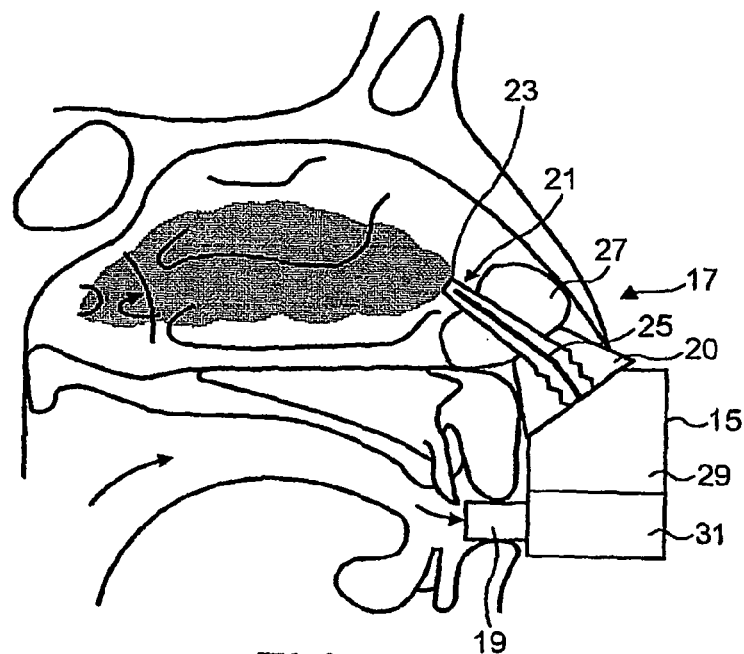
FIG. 4 schematically illustrates the delivery device of FIG. 2 during actuation.

Referring to FIG. 3, the nosepiece 17 is first inserted into one of the nasal cavities of a subject until the guide member 20 abuts the nares of the nostril, at which point the distal end of the outlet unit 21 extends about 2 cm into the nasal cavity of the subject, and the mouthpiece 19 is gripped in the lips of the subject.

The subject then begins to exhale through the mouthpiece 19, which exhalation acts to close the oropharyngeal velum of the subject and drive an air flow through the delivery channel 23 of the outlet unit 21, with the air flow passing into the one nasal cavity, around the posterior margin of the nasal septum and out of the other nasal cavity, thereby achieving a bi-directional air flow through the nasal airway of the subject. Exhalation through the mouthpiece 19 acts to develop a pressure in the delivery channel 23, which pressure acts to inflate the at least one cuff member 27. As illustrated in FIG. 4, the expansion of the at least one cuff member 27 acts to expand the nasal valve in the nasal cavity, seal the delivery channel 23 to the inner wall of the nasal cavity, and position the outlet unit 21 in relation to the nasal cavity of the subject. As will be noted from FIG. 4, the outlet unit 21 is forced to adopt the required position by the at least one cuff member 27, in this embodiment as accommodated by flexing of the outlet unit 21.

In this embodiment, when the flow rate developed through the delivery channel 23 reaches a predetermined value, the release mechanism 31 is triggered to actuate the substance supply unit 29 to deliver a metered dose of a substance to the nozzle 25 and into the nasal cavity of the subject. In the alternative embodiment the release mechanism 31 could be triggered on the generation of a predetermined pressure in the delivery channel 23.

Figure 5:
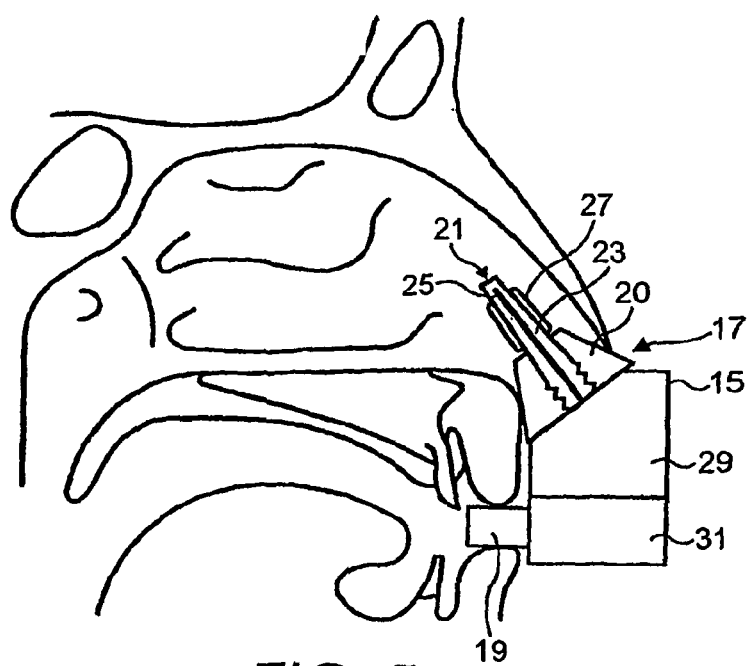
FIG. 5 schematically illustrates the delivery device of FIG. 2 following actuation.
Figure 6:
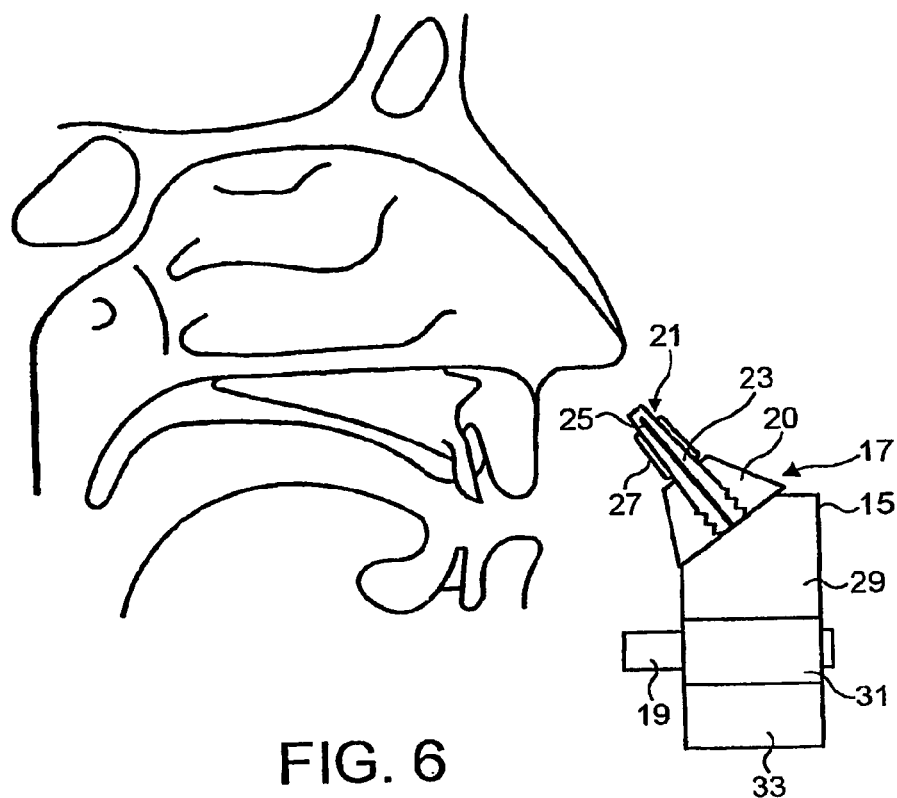
FIG. 6 schematically illustrates a nasal delivery device in accordance with a second embodiment of the present invention.
Figure 7:
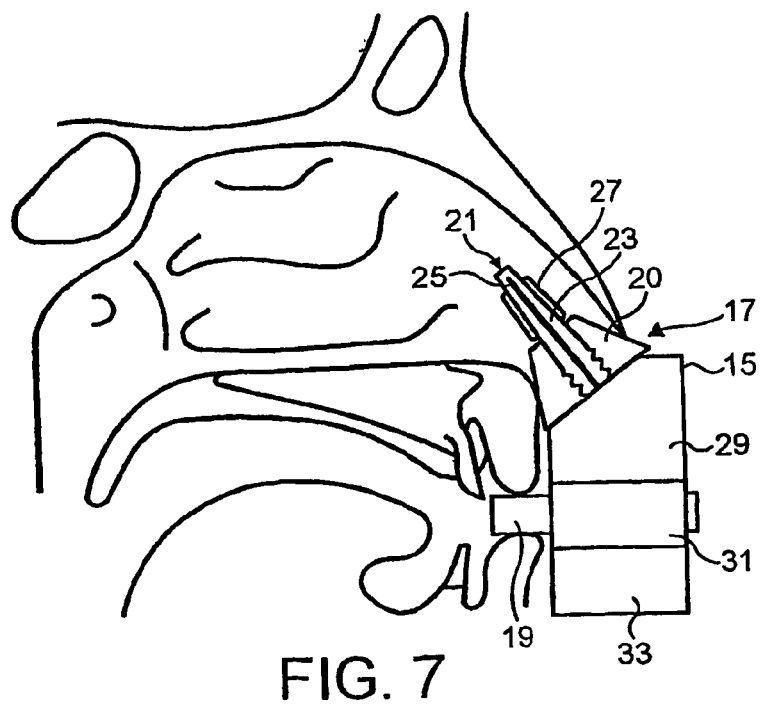
FIG. 7 schematically illustrates the delivery device of FIG. 6 inserted in a nasal cavity of a subject for operation.
Figure 8:
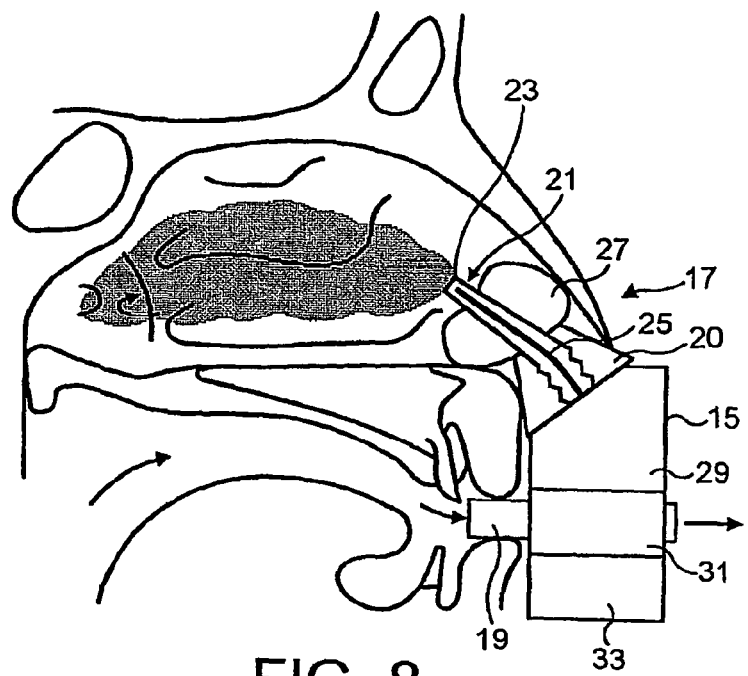
FIG. 8 schematically illustrates the delivery device of FIG. 6 during actuation.
Figure 9:
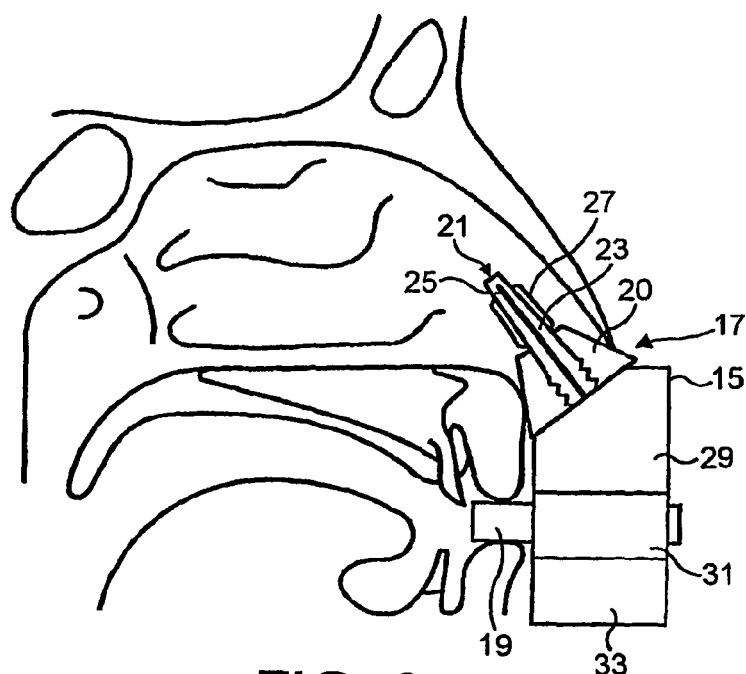
FIG. 9 schematically illustrates the delivery device of FIG. 6 following actuation.
Figure 10:
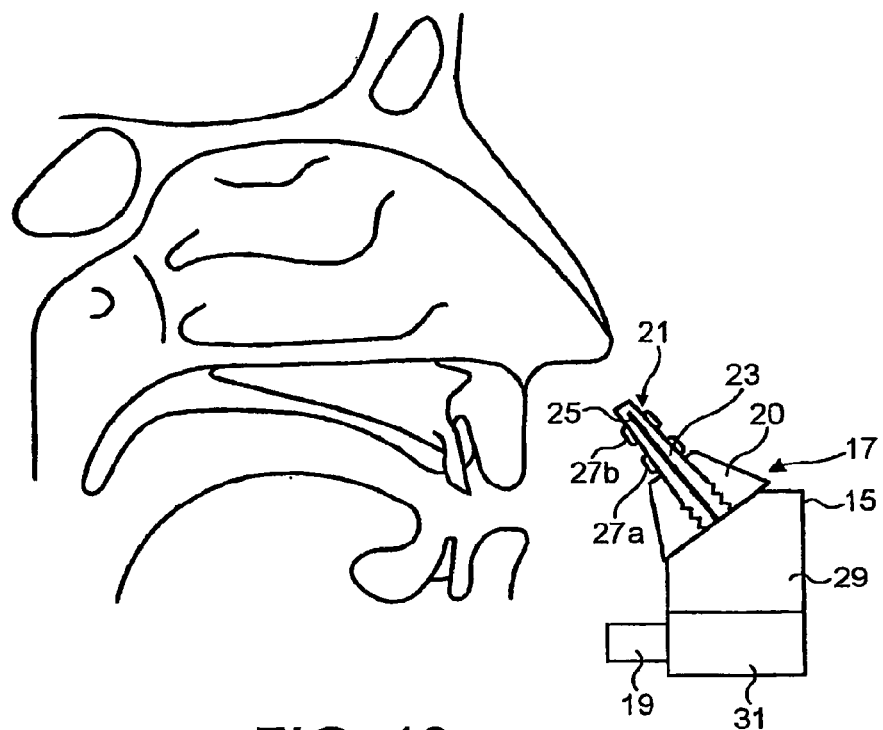
FIG. 10 schematically illustrates a nasal delivery device in accordance with a third embodiment of the present invention.
Figure 11:
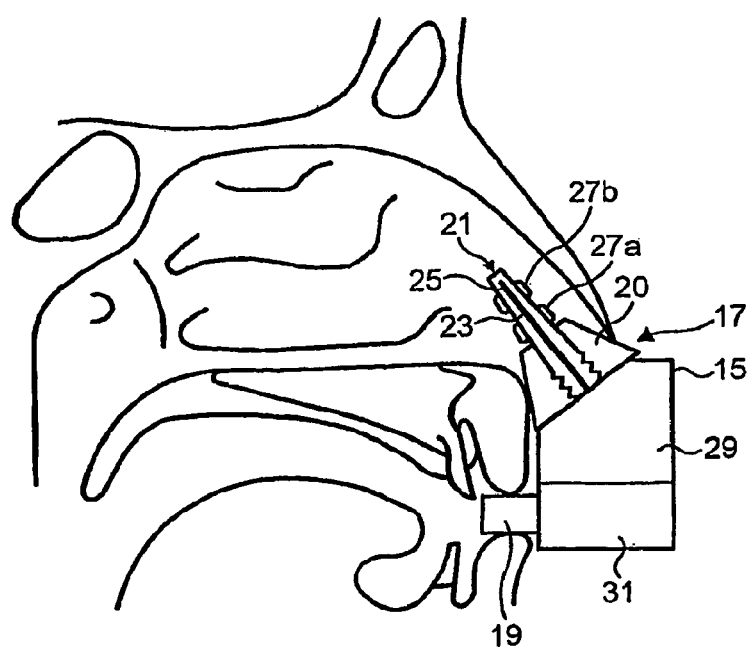
FIG. 11 schematically illustrates the delivery device of FIG. 10 inserted in a nasal cavity of a subject for operation.
Figure 12:
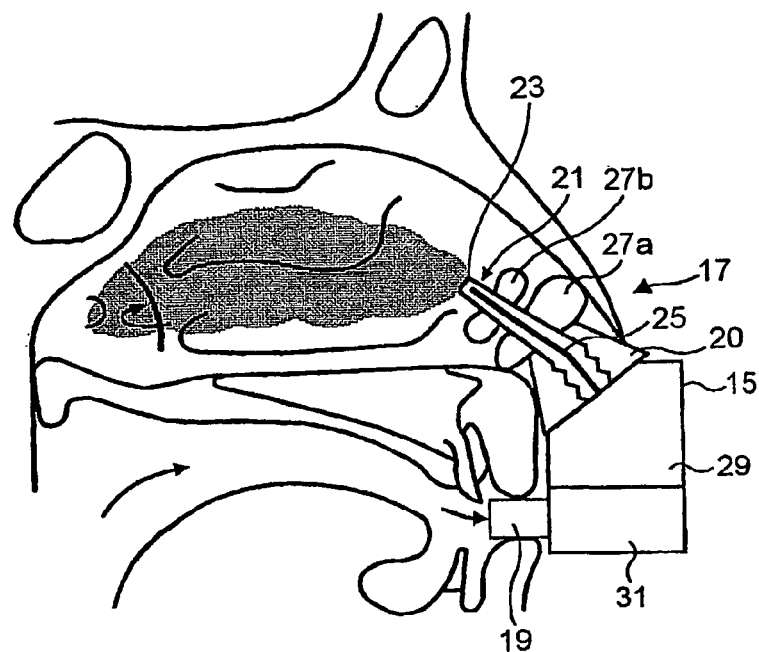
FIG. 12 schematically illustrates the delivery device of FIG. 10 during actuation.
Figure 13:
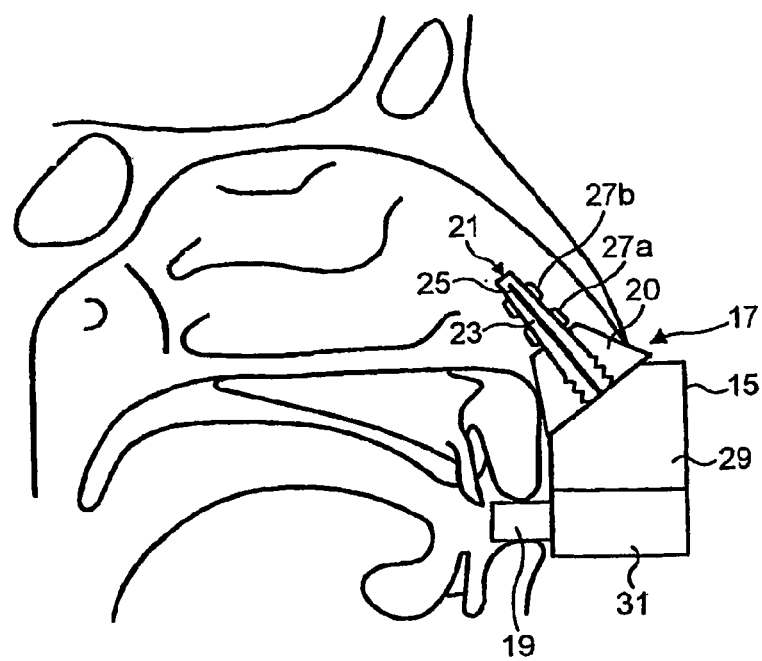
FIG. 13 schematically illustrates the delivery device of FIG. 2 following actuation.

Following exhalation, the pressure in the delivery channel 23 decreases and the at least one cuff member 27 deflates, as illustrated in FIG. 5, at which point the mouthpiece 19 is released and the nosepiece 17 withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 29. In a preferred embodiment, where the nosepiece 17 is replaceable, the nosepiece 17 can be replaced with a new nosepiece 17.

FIGS. 6 to 9 illustrate an exhalation breath-actuated nasal delivery device in accordance with a second embodiment of the present invention.

The delivery device of this embodiment is very similar to the delivery device of the above-described first embodiment, and thus, in order to avoid unnecessary duplication of description, only the differences will be described in detail, with like reference signs designating like parts The delivery device of this embodiment differs from that of the above-described first embodiment in further comprising an oral exhalation breath-actuatable gas supply unit 33 for delivering a gas flow through the delivery channel 23 of the outlet unit 21 in response to exhalation by a subject, and in that the mouthpiece 19 is in fluid communication with the gas supply unit 33 and not the delivery channel 23 of the outlet unit 21, whereby a gas flow is delivered to the delivery channel 23 of the outlet unit 21, and hence the nasal airway of the subject, in response to exhalation through the mouthpiece 19.

Operation of the delivery device is the same as for the above-described first embodiment, with a gas flow being delivered to the delivery channel 23 of the outlet unit 21 in response to exhalation through the mouthpiece 19.

FIGS. 10 to 13 illustrate an exhalation breath-actuated nasal delivery device in accordance with a third embodiment of the present invention.

The delivery device of this embodiment is very similar to the delivery device of the above-described first embodiment, and thus, in order to avoid unnecessary duplication of description, only the differences will be described in detail, with like reference signs designating like parts.

The delivery device of this embodiment differs from that of the above-described first embodiment only in that the nosepiece 17 comprises a plurality of, in this embodiment two, inflatable cuff members 27a, 27b. This arrangement of cuff members 27a, 27b enables the distalmost cuff member 27b to have a reduced size, and thereby facilitates insertion of the outlet unit 21 through the narrow nasal valve in the nasal cavity of the subject.

Operation of the delivery device is the same as for the above-described first embodiment.

Figure 14:
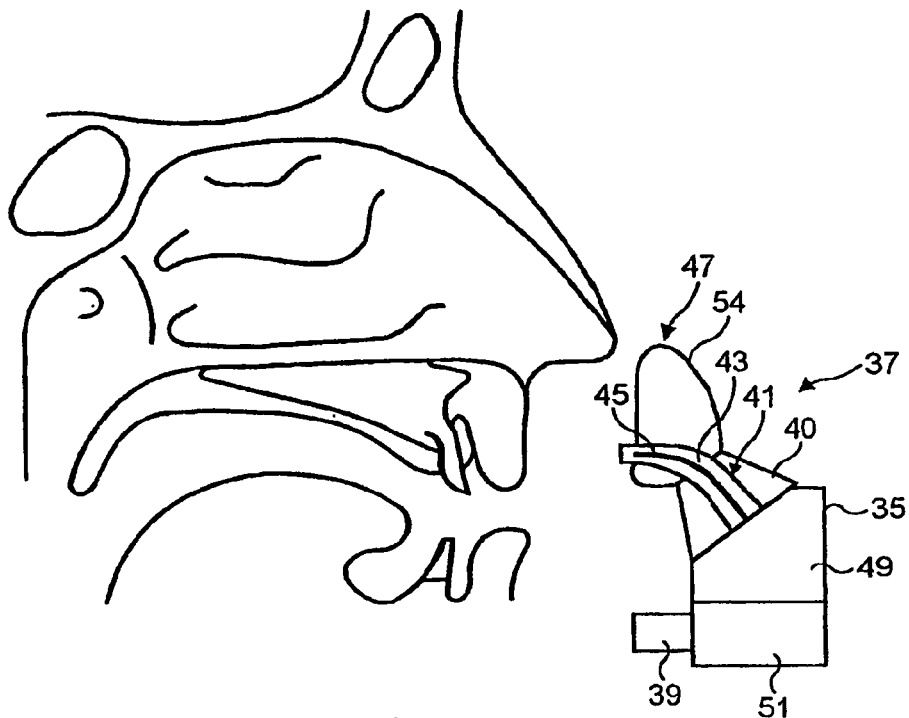
FIG. 14 schematically illustrates a nasal delivery device in accordance with a fourth embodiment of the present invention.
Figure 15:
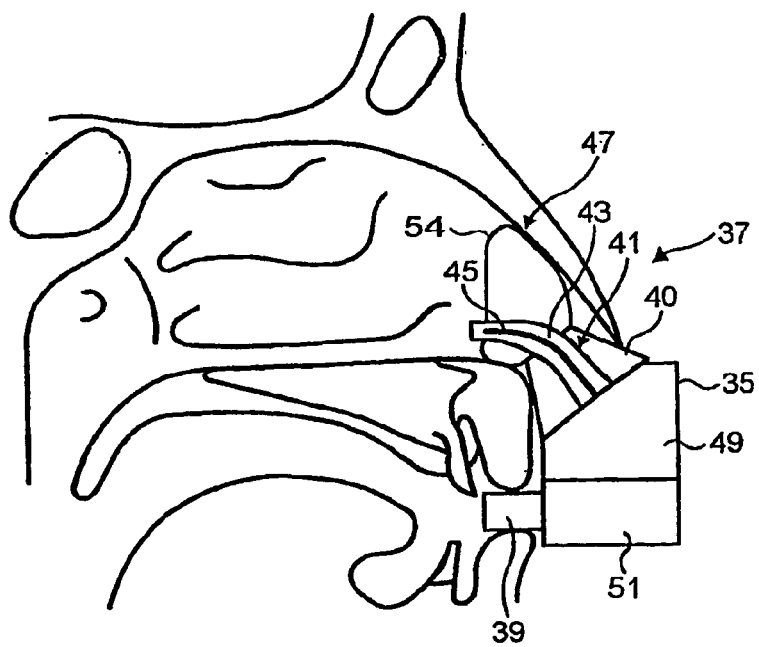
FIG. 15 schematically illustrates the delivery device of FIG. 14 inserted in a nasal cavity of a subject for operation.
Figure 16:
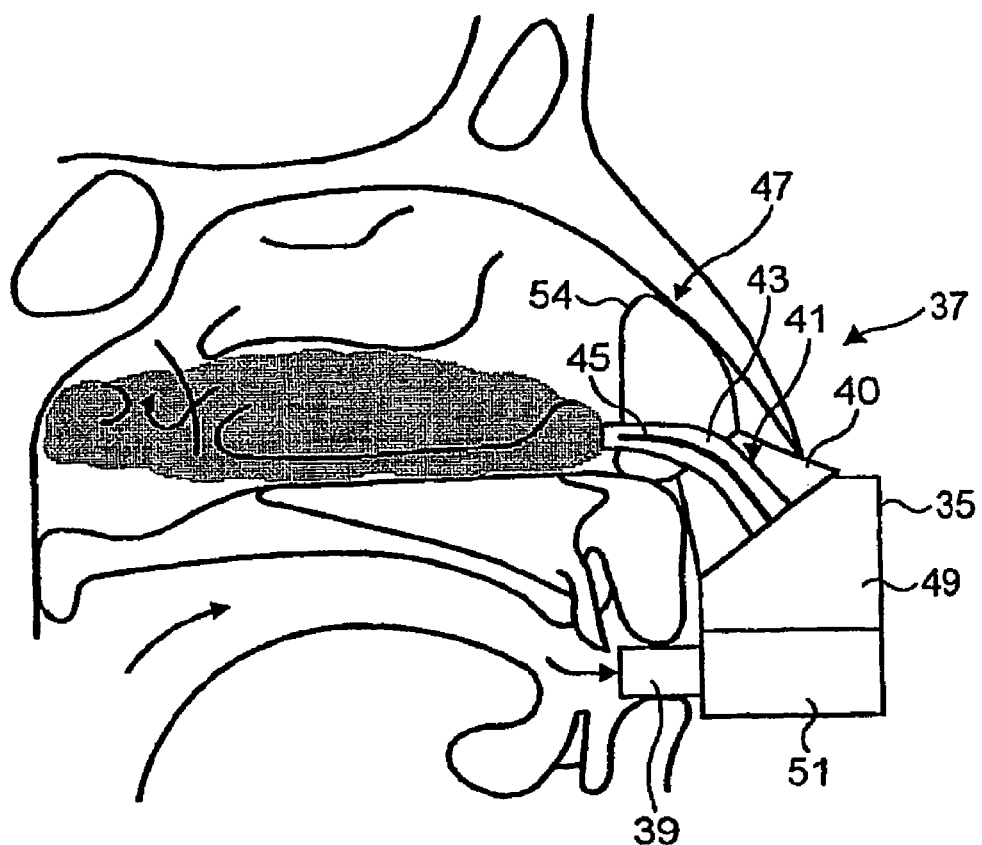
FIG. 16 schematically illustrates the delivery device of FIG. 14 during actuation.

FIGS. 14 to 16 illustrate an exhalation breath-actuated nasal delivery device in accordance with a fourth embodiment of the present invention.

The delivery device comprises a housing 35, a nosepiece 37 for fitting in a nasal cavity of a subject, and a mouthpiece 39 through which the subject exhales to actuate the delivery device.

The nosepiece 37 comprises a guide member 40, in this embodiment a frusto-conical element, for guiding the nosepiece 37 into the nasal cavity of the subject, and an outlet unit 41 for delivering substance into the nasal airway of the subject. In this embodiment the nosepiece 37 is a replaceable unit.

In this embodiment the outlet unit 41 comprises a delivery channel 43 which is in fluid communication with the mouthpiece 39 such that an air flow is delivered into and through the nasal airway of the subject on exhalation by the subject through the mouthpiece 39, and a nozzle 45 for delivering substance into the nasal cavity of the subject. In this embodiment the nozzle 45 is disposed in the delivery channel 43 co-axially with the same. In this embodiment the nozzle 45 is configured to provide an aerosol spray. In an alternative embodiment, for the delivery of a liquid, the nozzle 45 could be configured to deliver a liquid jet as a column of liquid.

In this embodiment at least the tip of the delivery channel 43 comprises a tubular section of a flexible, preferably resilient, material. In a preferred embodiment the material is a semi-soft plastics material, such as silicone rubber.

In this embodiment at least the tip of the delivery channel 43 has a tapering section which narrows to the distal end thereof. The delivery channel 43, in having a narrowing taper, acts, on insertion, to expand the narrow nasal valve of the nasal cavity of the subject. In a preferred embodiment the delivery channel 43 has an elliptical section, preferably an oval section.

In a preferred embodiment the outlet unit 41 is configured to extend at least about 2 cm, preferably at least about 3 cm, and more preferably from about 2 cm to about 3 cm, into the nasal cavity of the subject.

The nosepiece 37 further comprises at least one cuff member 47 for fitting in the nasal cavity of the subject. In this embodiment the at least one cuff member 47 is a resilient member which is deformable to allow for insertion into the nasal cavity of the subject and, on insertion, expansion to adopt the required position in the nasal cavity, in which position the outlet unit 41 is correctly positioned. When so positioned, the at least one cuff member 47 provides for the expansion of the narrow nasal valve in the nasal cavity, the sealing of the outlet unit 41 in the nasal cavity, and the positioning, in particular the direction, of the outlet unit 41 in the nasal cavity of the subject. In this embodiment the at least one cuff member 47 comprises a sponge member, here a foam member. In an alternative embodiment the at least one cuff member 47 could comprise a gel-filled member, such as a silicone-filled member.

In this embodiment the at least one cuff member 47 is configured such that, when inserted in the nasal cavity, the outlet unit 41 is directed at a lower region of the nasal cavity of the subject. In preferred embodiments the at least one cuff member 47 can be configured to direct the outlet unit 41 at any region of the inferior meatus and the inferior region of the middle meatus, whereby substance can be targeted in particular at the inferior nasal concha, and the adenoids and tubal ostia in the superior region of the epipharynx.

Regions in the nasal airway adjacent the inferior meatus and the inferior region of the middle meatus represent the regions in the nasal airway which provide the path of least flow resistance therethrough. With existing nasal spray systems, the delivery is such that the delivered substance flows along the floor of the nasal cavity, with the result that the substance does not reach the adenoids or the tubal ostia.

In this embodiment the at least one cuff member 47 includes at least one lobe 54, here a single lobe 54, which is configured such as to extend into, and thereby obstruct, an upper region of the nasal cavity of the subject, the at least one lobe 54 acting to force the delivered flow to follow a flow path defined by the inferior meatus and the inferior region of the middle meatus. The achievement of such a flow path, allied with an optimization of the particle size distribution, provides that a much larger fraction of substance can be delivered to sites in the inferior meatus and the inferior region of the middle meatus.

In this embodiment the at least one cuff member 47 comprises a single annular cuff member 47 which is disposed about the outlet unit 41.

In an alternative embodiment the at least one cuff member 47 could comprise a plurality of cuff members 47 which are disposed about the outlet unit 41.

The delivery device further comprises a substance supply unit 49 for delivering metered doses of a substance, in this embodiment an aerosol canister for delivering metered volumes of a propellant, preferably a hydrofluoroalkane (HFA) propellant or the like, containing medicament, either as a suspension or solution, which is fluidly connected to the nozzle 45 to deliver substance from the nosepiece 37, in this embodiment as an aerosol spray.

In this embodiment the substance supply unit 49 is a multi-dose unit for delivering a plurality of metered doses of substance. In another embodiment the substance supply unit 49 could be a single-dose unit for delivering a single metered dose of substance.

The substance supply unit 49 is pre-primeable, in this embodiment by loading a resilient element, and includes a breath-actuated release mechanism 51 which, when triggered, releases the resilient element and actuates the substance supply unit 49 to deliver a metered dose of a substance through the nozzle 45.

In this embodiment the trigger mechanism 51 is configured to cause actuation of the substance supply unit 49 on generation of a predetermined flow rate through the delivery channel 43.

In another embodiment the trigger mechanism 51 could be configured to cause actuation of the substance supply unit 49 on generation of a predetermined pressure within the delivery channel 43.

In a further embodiment the trigger mechanism 51 could be configured to cause actuation of the substance supply unit 49 on generation of either one of a predetermined flow rate through the delivery channel 43 or a predetermined pressure within the delivery channel 43.

In an alternative embodiment the substance supply unit 49 could comprise a mechanical delivery pump, in particular a liquid delivery pump or a powder delivery pump, which delivers metered doses of a substance on actuation thereof.

In another alternative embodiment the substance supply unit 49 could comprise a dry powder delivery unit which delivers metered doses of a substance, as a dry powder, on actuation thereof.

In yet another alternative embodiment the substance supply unit 49 could comprise a nebulizer which delivers metered doses of a substance, as an aerosol spray, on actuation thereof.

Operation of the delivery device will now be described hereinbelow with reference to FIGS. 15 and 16 of the accompanying drawings.

Referring to FIG. 15, the nosepiece 37 is first inserted into a nasal cavity of a subject until the guide member 40 abuts the nares of the nostril, at which point the distal end of the outlet unit 41 extends about 2 cm into the nasal cavity of the subject, and the mouthpiece 39 is gripped in the lips of the subject.

The subject then begins to exhale through the mouthpiece 39, which exhalation acts to close the oropharyngeal velum of the subject and drive an air flow through the delivery channel 43 of the outlet unit 41, with the air flow passing into the one nasal cavity, around the posterior margin of the nasal septum and out of the other nasal cavity, thereby achieving a bi-directional air flow through the nasal airway of the subject.

In this embodiment, when the flow rate developed through the delivery channel 43 reaches a predetermined value, the release mechanism 51 is triggered to actuate the substance supply unit 49 to deliver a metered dose of a substance to the nozzle 45 and into the nasal cavity of the subject. In the alternative embodiment the release mechanism 51 could be triggered on the generation of a predetermined pressure in the delivery channel 43.

Following exhalation, the mouthpiece 39 is released and the nosepiece 37 withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 49. In a preferred embodiment, where the nosepiece 37 is replaceable, the nosepiece 37 can be replaced with a new nosepiece 37.

Figure 17:
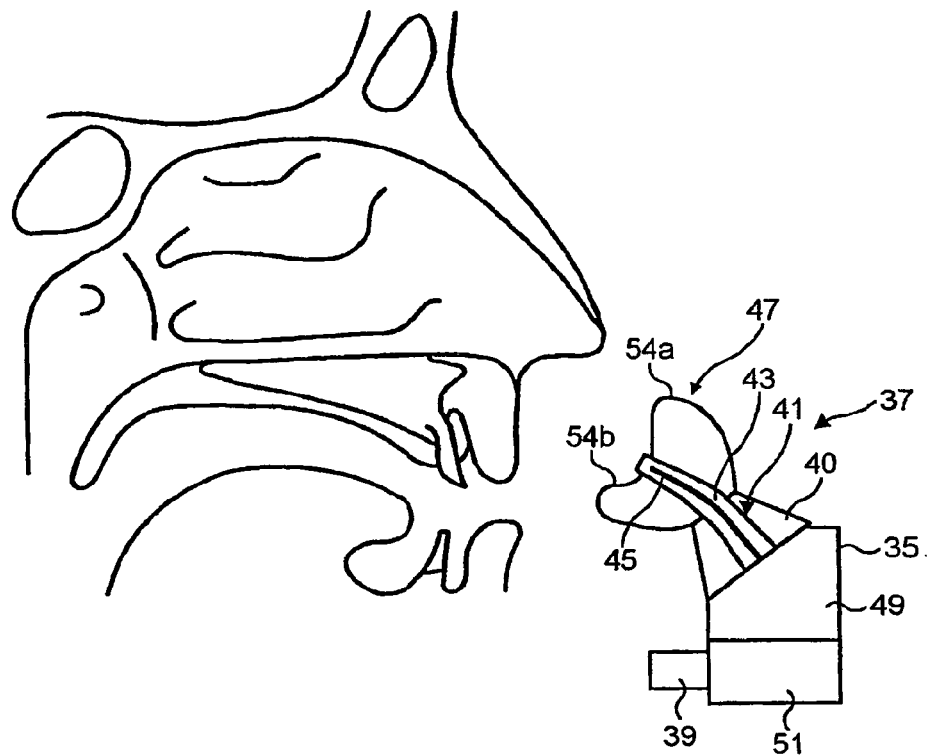
FIG. 17 schematically illustrates a nasal delivery device in accordance with a fifth embodiment of the present invention.
Figure 18:
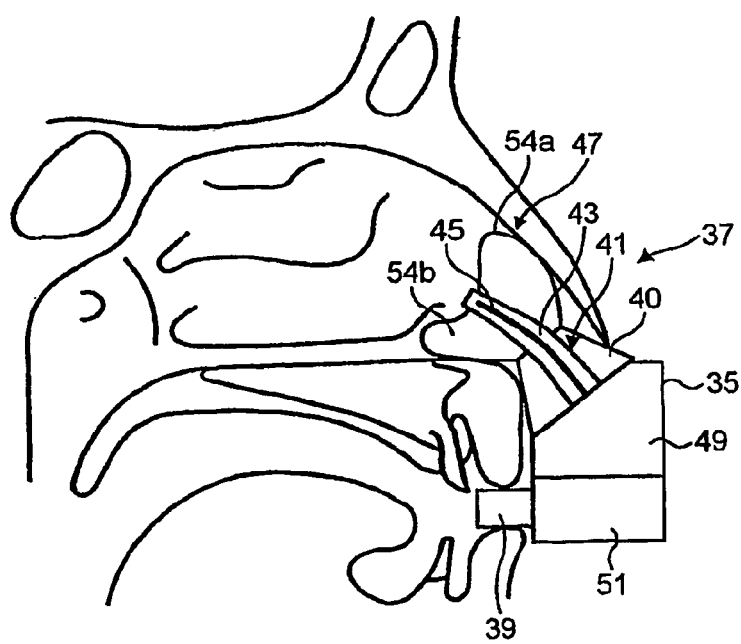
FIG. 18 schematically illustrates the delivery device of FIG. 17 inserted in a nasal cavity of a subject for operation.
Figure 19:
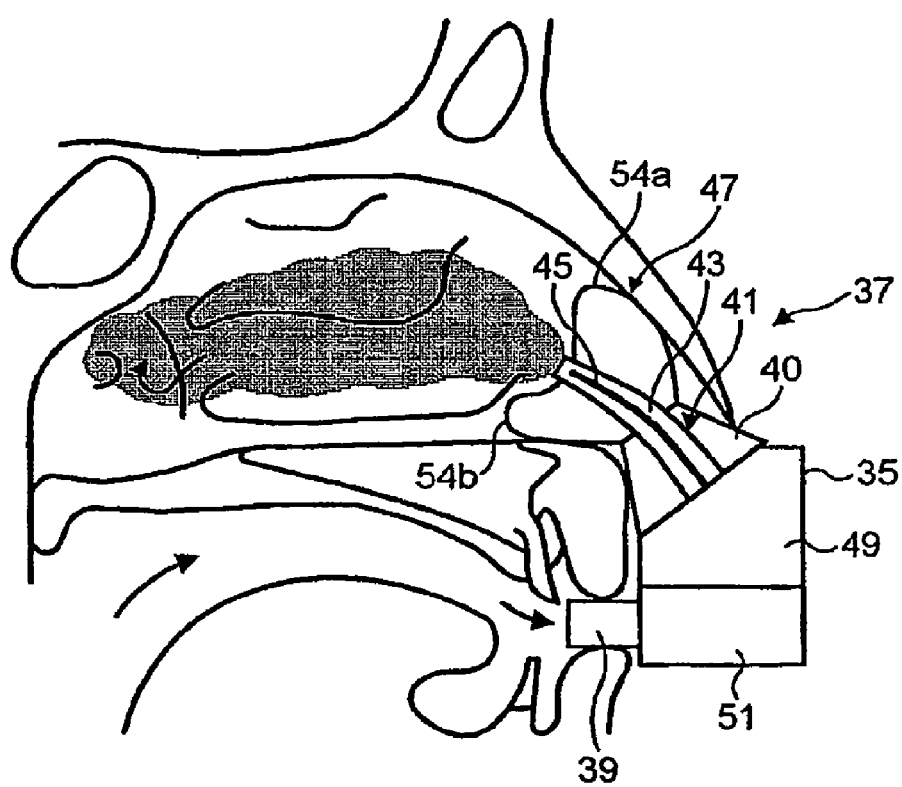
FIG. 19 schematically illustrates the delivery device of FIG. 17 during actuation.
Figure 20:
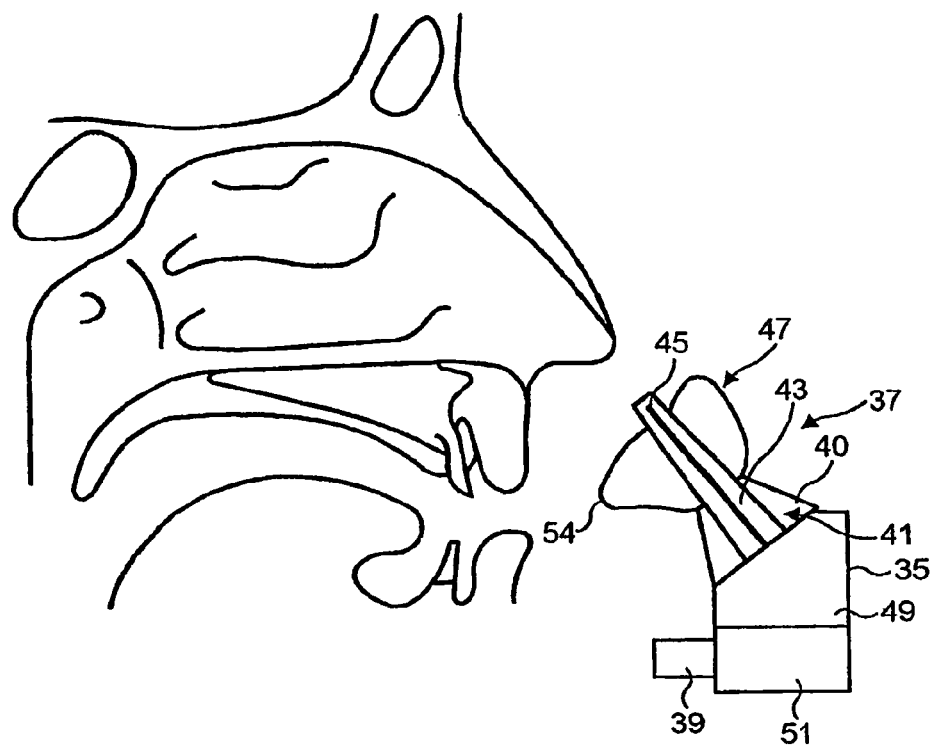
FIG. 20 schematically illustrates a nasal delivery device in accordance with a sixth embodiment of the present invention.
Figure 21:
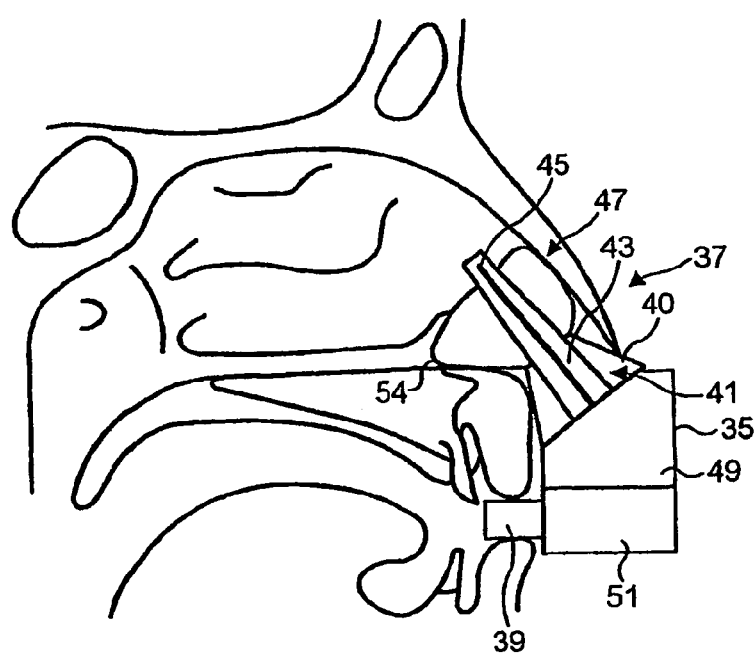
FIG. 21 schematically illustrates the delivery device of FIG. 20 inserted in a nasal cavity of a subject for operation.
Figure 22:
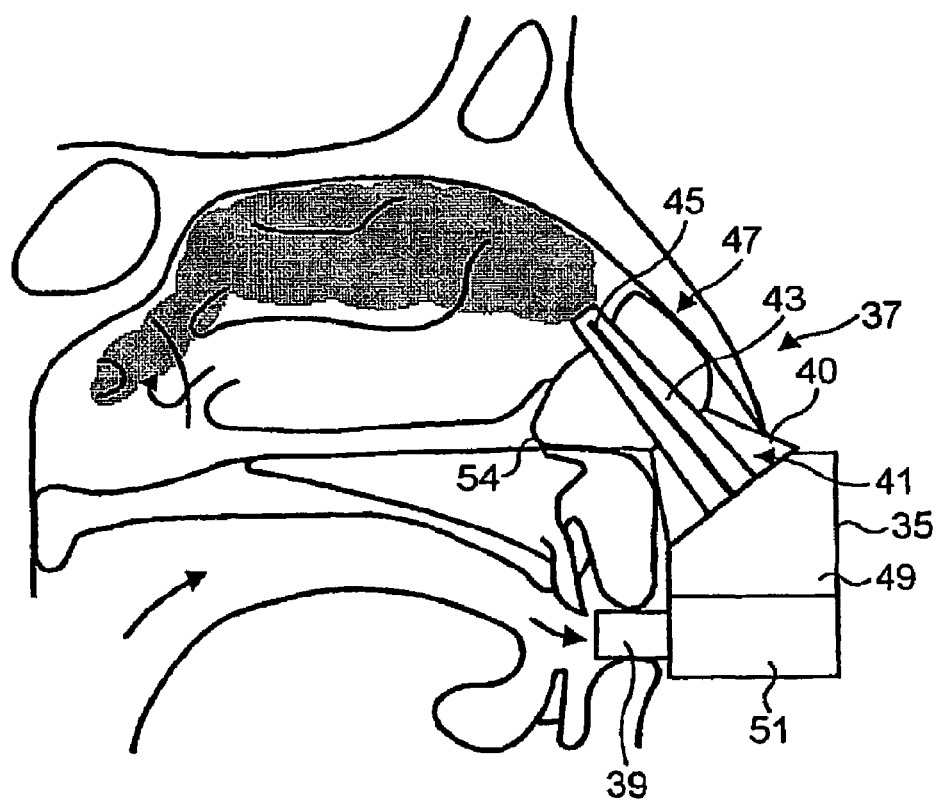
FIG. 22 schematically illustrates the delivery device of FIG. 20 during actuation.
Figure 23:
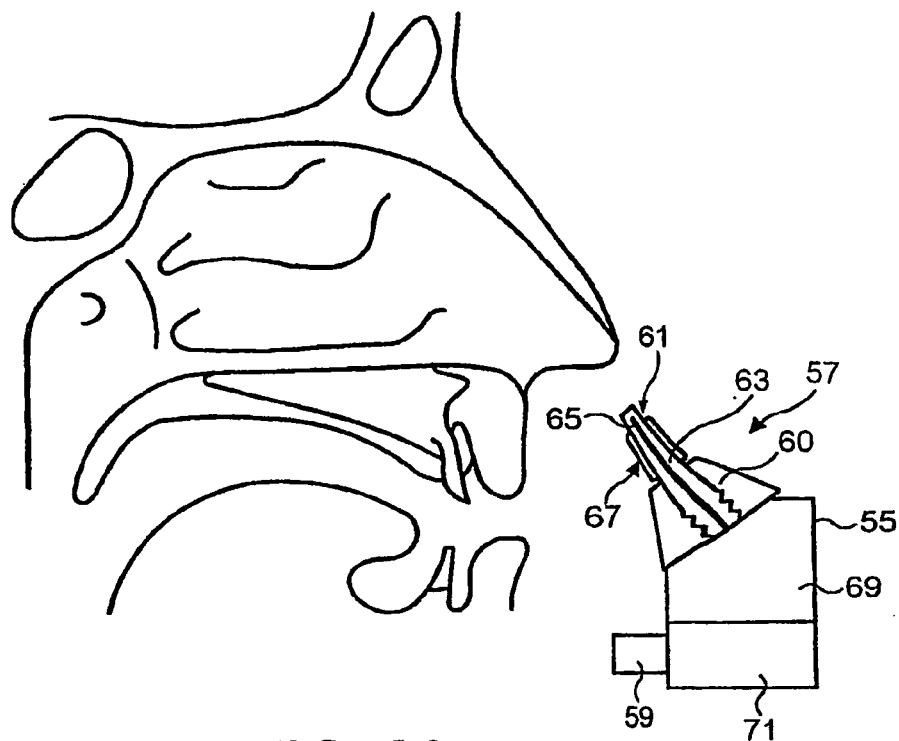
FIG. 23 schematically illustrates a nasal delivery device in accordance with a seventh embodiment of the present invention.

FIGS. 17 to 19 illustrate an exhalation breath-actuated nasal delivery device in accordance with a fifth embodiment of the present invention.

The delivery device of this embodiment is very similar to the delivery device of the above-described fourth embodiment, and thus, in order to avoid unnecessary duplication of description, only the differences will be described in detail, with like reference signs designating like parts.

The delivery device of this embodiment differs from that of the above-described fourth embodiment only in the configuration of the outlet unit 41 and the at least one cuff member 47.

In this embodiment the at least one cuff member 47 is configured such that, when inserted in the nasal cavity of the subject, the outlet unit 41 is directed at a middle region of the nasal cavity of the subject. In a preferred embodiment the at least one cuff member 47 can be configured to direct the outlet unit 41 at any region of the middle meatus and the inferior region of the superior meatus, whereby substance can be targeted in particular at the middle nasal concha, the sinus infundibulum and the sinus ostia.

The middle meatus is the region of the nasal cavity located under and lateral to the middle nasal concha, with the sinus infundibulum and the sinus ostia representing the sites of the main pathologies in many very common diseases, such as chronic sinusitis, which affects about 10 to 15% of the population and has no FDA approved treatment, and nasal polyposis. The only known treatment of these conditions is the application of drops during a rigorous and complex procedure involving severe neck extension and the so-called "Mecca" position. As will be appreciated, however, owing to the complicated and often painful procedure, compliance is very poor. Existing nasal spray systems are ineffective in delivering substance to this region of the nasal cavity.

In this embodiment the at least one cuff member 47 includes upper and lower lobes 54*a*, 54*b* which are configured such as to extend into, and thereby obstruct, respective ones of the upper and lower regions of the nasal cavity of the subject, the lobes 54*a*, 54*b* acting to force a delivered flow to follow a flow path defined by the middle meatus and the inferior region of the superior meatus. The achievement of such a flow path, allied with an optimization of the particle size distribution, provides that a much larger fraction of substance can be delivered to sites in the middle meatus and the inferior region of the middle meatus.

Operation of the delivery device is the same as for the above-described fourth embodiment.

FIGS. 20 to 22 illustrate an exhalation breath-actuated nasal delivery device in accordance with a sixth embodiment of the present invention.

The delivery device of this embodiment is very similar to the delivery device of the above-described fourth embodiment, and thus, in order to avoid unnecessary duplication of description, only the differences will be described in detail, with like reference signs designating like parts.

The delivery device of this embodiment differs from that of the above-described fourth embodiment only in the configuration of the outlet unit 41 and the at least one cuff member 47.

In this embodiment the at least one cuff member 47 is configured such that, when inserted in the nasal cavity of the subject, the outlet unit 41 is directed at a superior region of the nasal cavity of the subject. In a preferred embodiment the at least one cuff member 47 can be configured to direct the outlet unit 41 at any region of the superior meatus, and in particular provide for the targeting of the superior nasal concha and the olfactory region.

The olfactory region is located in the superior region of the nasal cavity and typically has a surface area of from about 4 to 6 $cm^2$. The olfactory region represents the only region where it is possible to circumvent the blood-to-brain barrier (BBB) and enable communication with the cerebrospinal fluid (CSF) and the brain. Such delivery is necessary to enable effective treatment of neurological diseases, such as Alzheimer’s and Parkinson’s disease, psychiatric diseases and intracerebral infections.

The olfactory region is reached through narrow slit-like passages and the delivery of substance to this region is not possible using existing nasal delivery systems.

In existing nasal spray systems, substantially all of the particles are far too large to pass through the passages in communication with the olfactory region. Indeed, such spray systems are specifically designed to deliver particles having an average diameter of greater than 10 μm in order to comply with the FDA requirements which require that the maximum fraction of particles having a diameter of less than 10 μm be 5% of the total fraction. The reason for this requirement is that, where the velum is not closed, as would be the case where a subject inhales through the nose as prescribed for delivery, particles having a diameter of less than 10 μm could escape from the nasal cavity and be inhaled into the lungs.

In addition, in existing nasal spray systems, the flow characteristics of particles delivered into the nasal cavity are not suited to enable delivery through the passages communicating with the olfactory region.

Furthermore, the sniffing action by a subject during delivery causes the particles to be drawn into the inferior and middle regions of the nasal cavity, where the flow resistance is the lowest, with only a minimal fraction, if any, of the particles being delivered to the olfactory region.

In this embodiment, by ensuring closure of the velum in delivery and optimizing both the particle size distribution so as to include a larger fraction of smaller particles, typically having a particle size of less than 10 and the aerodynamic delivery conditions, the delivery device provides for the effective delivery of substance to the olfactory region. Such a delivery regime has not previously been known, and has been recognised by the present applicant as providing an improved delivery device and delivery method.

In this embodiment the at least one lobe 54 of the at least one cuff member 47 is configured such as to extend into, and thereby obstruct, a lower region of the nasal cavity of the subject, the at least one lobe 54 acting to force a delivered flow to follow a flow path defined by the superior meatus and in particular the olfactory region. The achievement of such a flow path, allied with an optimization of the particle size distribution, provides that a much larger fraction of substance can be delivered to sites in the superior meatus and in particular the olfactory region.

Operation of the delivery device is the same as for the above-described fourth embodiment.

FIGS. 23 to 26 illustrate an exhalation breath-actuated nasal delivery device in accordance with a seventh embodiment of the present invention.

The delivery device comprises a housing 55, a nosepiece 57 for fitting in a nasal cavity of a subject, and a mouthpiece 59 through which the subject exhales to actuate the delivery device.

The nosepiece 57 comprises a guide member 60, in this embodiment a frusto-conical element, for guiding the nosepiece 57 into a nasal cavity of the subject, and an outlet unit 61 for delivering substance into the nasal airway of the subject. In this embodiment the nosepiece 57 is a replaceable unit.

In this embodiment the outlet unit 61 comprises a delivery channel 63 which is in fluid communication with the mouthpiece 59 such that an air flow is delivered into and through the nasal airway of the subject on exhalation by the subject through the mouthpiece 59, and a nozzle 65 for delivering substance to the nasal airway of the subject. In this embodiment the nozzle 65 is disposed in the delivery channel 63 co-axially with the same. In this embodiment the nozzle 65 is configured to provide an aerosol spray. In an alternative embodiment, for the delivery of a liquid, the nozzle 65 could be configured to deliver a liquid jet as a column of liquid.

In this embodiment the outlet unit 61 is movably coupled to the housing 55, here as provided by a flexible coupling, such as to allow for the positioning of the outlet unit 61 in the nasal cavity of the subject, as will be described in more detail hereinbelow.

In an alternative embodiment the outlet unit 61 could be fixed to the housing 55, and the mouthpiece 59 instead movably coupled to the housing 55, here as provided by a flexible coupling, such as to allow for the positioning of the outlet unit 61 in the nasal cavity of the subject.

In this embodiment at least the tip of the delivery channel 63 comprises a tubular section of a flexible, preferably resilient, material. In a preferred embodiment the material is a semi-soft plastics material, such as silicone rubber.

In this embodiment at least the tip of the delivery channel 63 has a tapering section which narrows to the distal end thereof. The delivery channel 63, in having a narrowing taper, acts, on insertion, to expand the narrow nasal valve of the nasal cavity of the subject. In a preferred embodiment the delivery channel 63 has an elliptical section, preferably an oval section.

In a preferred embodiment the distal end of the outlet unit 61 is configured to extend at least about 2 cm, preferably at least about 3 cm, and more preferably from about 2 cm to about 3 cm, into the nasal cavity of the subject.

The nosepiece 57 further comprises at least one expandable cuff member 67 for expansion in the nasal cavity of the subject. In this embodiment the at least one cuff member 67 comprises an inflatable member.

In this embodiment the at least one cuff member 67 is in fluid communication with the delivery channel 63, whereby the air flow generated by the subject on exhalation through the mouthpiece 59 acts to inflate the at least one cuff member 67. In an alternative embodiment the delivery device could include a separate pump unit for inflating the at least one cuff member 67 subsequent to fitting of the nosepiece 57, and in a preferred embodiment subsequent to, preferably in response to, exhalation through the mouthpiece 59.

In this embodiment the at least one cuff member 67 is an inflatable member which is inflated on exhalation by the subject. In an alternative embodiment the at least one cuff member 67 could be inflated on the nosepiece 57 being located in the correct position.

In this embodiment the at least one cuff member 67 comprises a flexible balloon element which is inflated by the generation of a pressure in the delivery channel 63, with the at least one cuff member 67 deflating on the release of pressure from the delivery channel 63. In the alternative embodiment, where the at least one cuff member 67 is inflated by a separate pump unit, the at least one cuff member 67 could equally be deflated by the evacuation of gas therefrom using the same pump unit.

In one embodiment the at least one cuff member 67 could comprise a resilient balloon element which is inflated by the generation of a pressure in the delivery channel 63, with the at least one cuff member 67 returning to the original, deflated configuration on the release of pressure from the delivery channel 63.

In another embodiment the at least one cuff member 67 could comprise an inflatable sponge element, in one embodiment a foam element having an encapsulating sealing layer, which can be compressed, in this embodiment by evacuation, to adopt a compact configuration to allow for insertion into a nasal cavity of the subject and inflated, in this embodiment by breaking the vacuum, to allow for the introduction of a gas into the porous structure of the sponge element. In one embodiment such a cuff member 67 could be in selective fluid communication with the atmosphere. In another embodiment such a cuff member 67 could be in selective fluid communication with the delivery channel 63, whereby the pressure developed in the delivery channel 63 would assist in the inflation of the cuff member 67. In the alternative embodiment which includes a separate pump unit, the pump unit could be employed to assist in inflating such a cuff member 67 and in deflating the cuff member 67 by the evacuation of gas therefrom. In one embodiment the inflation could be triggered on exhalation by the subject. In another embodiment the inflation could be triggered on the nosepiece 57 being located in the correct position in the nasal cavity of the subject.

The at least one cuff member 67 is disposed to an outer surface of the outlet unit 61 such as, on expansion, to engage the inner wall of the nasal cavity of the subject. The at least one cuff member 67, in being expandable, provides for the expansion of the narrow nasal valve of the nasal cavity of the subject, the sealing of the nosepiece 57 in the nasal cavity of the subject, and the positioning, in particular the direction, of the outlet unit 61 in the nasal cavity of the subject.

In this embodiment the at least one cuff member 67 comprises a single annular cuff member 67 which is located about the outlet unit 61 such as to provide a seal between the delivery channel 63 and the inner wall of the nasal cavity of the subject when inflated.

In an alternative embodiment the at least one cuff member 67 could comprise a plurality of cuff members 67 which together provide a seal between the delivery channel 63 and the inner wall of the nasal cavity of the subject when inflated.

In this embodiment the at least one cuff member 67 is configured such that, when inserted in the nasal cavity, the outlet unit 61 is directed at a lower region of the nasal cavity of the subject. In preferred embodiments the at least one cuff member 67 can be configured to direct the outlet unit 61 at any region of the inferior meatus and the inferior region of the middle meatus, whereby substance can be targeted in particular at the inferior nasal concha, and the adenoids and tubal ostia in the superior region of the epipharynx.

Regions in the nasal airway adjacent the inferior meatus and the inferior region of the middle meatus represent the regions in the nasal airway which provide the path of least flow resistance therethrough. With existing nasal spray systems, the delivery is such that the delivered substance flows along the floor of the nasal cavity, with the result that the substance does not reach the adenoids or the tubal ostia.

In this embodiment the at least one cuff member 67 includes at least one lobe 74, here a single lobe 74, which is configured such as to extend into, and thereby obstruct, an upper region of the nasal cavity of the subject, the at least one lobe 74 acting to force the delivered flow to follow a flow path defined by the inferior meatus and the inferior region of the middle meatus. The achievement of such a flow path, allied with an optimization of the particle size distribution, provides that a much larger fraction of substance can be delivered to sites in the inferior meatus and the inferior region of the middle meatus.

In this embodiment the at least one cuff member 67 comprises a single annular cuff member 67 which is disposed about the outlet unit 61.

In an alternative embodiment the at least one cuff member 67 could comprise a plurality of cuff members 67 which are disposed about the outlet unit 61.

The delivery device further comprises a substance supply unit 69 for delivering metered doses of a substance, in this embodiment an aerosol canister for delivering metered volumes of a propellant, preferably a hydrofluoroalkane (HFA) propellant or the like, containing medicament, either as a suspension or solution, which is fluidly connected to the nozzle 65 to deliver substance from the nosepiece 57, in this embodiment as an aerosol spray.

In this embodiment the substance supply unit 69 is a multi-dose unit for delivering a plurality of metered doses of substance. In another embodiment the substance supply unit 69 could be a single-dose unit for delivering a single metered dose of substance.

The substance supply unit 69 is pre-primeable, in this embodiment by loading a resilient element, and includes a breath-actuated release mechanism 71 which, when triggered, releases the resilient element and actuates the substance supply unit 69 to deliver a metered dose of a substance through the nozzle 65.

In this embodiment the trigger mechanism 71 is configured to cause actuation of the substance supply unit 69 on generation of a predetermined flow rate through the delivery channel 63.

In another embodiment the trigger mechanism 71 could be configured to cause actuation of the substance supply unit 69 on generation of a predetermined pressure within the delivery channel 63.

In a further embodiment the trigger mechanism 71 could be configured to cause actuation of the substance supply unit 69 on generation of either one of a predetermined flow rate through the delivery channel 63 or a predetermined pressure within the delivery channel 63.

In an alternative embodiment the substance supply unit 69 could comprise a mechanical delivery pump, in particular a liquid delivery pump or a powder delivery pump, which delivers metered doses of a substance on actuation thereof.

In another alternative embodiment the substance supply unit 69 could comprise a dry powder delivery unit which delivers metered doses of a substance, as a dry powder, on actuation thereof.

In yet another alternative embodiment the substance supply unit 69 could comprise a nebulizer which delivers metered doses of a substance, as an aerosol spray, on actuation thereof.

Operation of the delivery device will now be described hereinbelow with reference to FIGS. 24 to 26 of the accompanying drawings.

Figure 24:
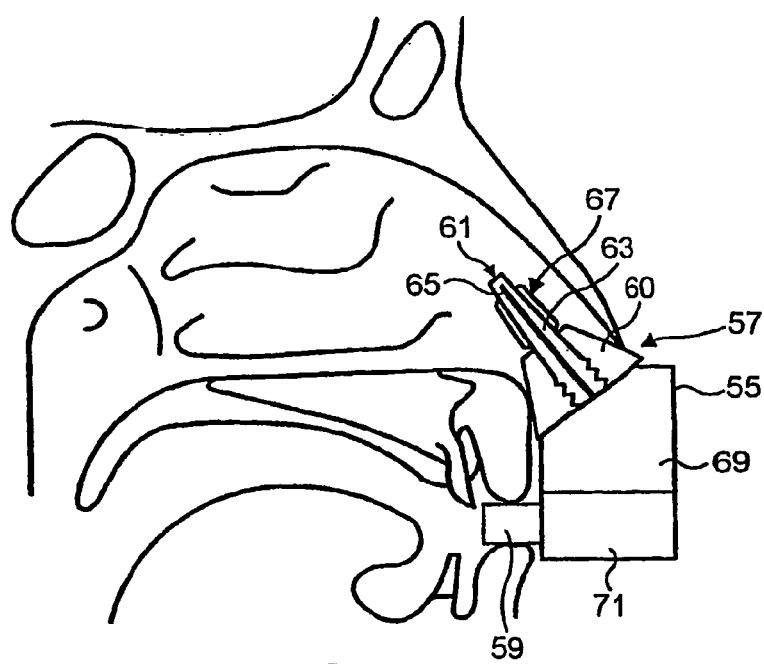
FIG. 24 schematically illustrates the delivery device of FIG. 23 inserted in a nasal cavity of a subject for operation.
Figure 25:
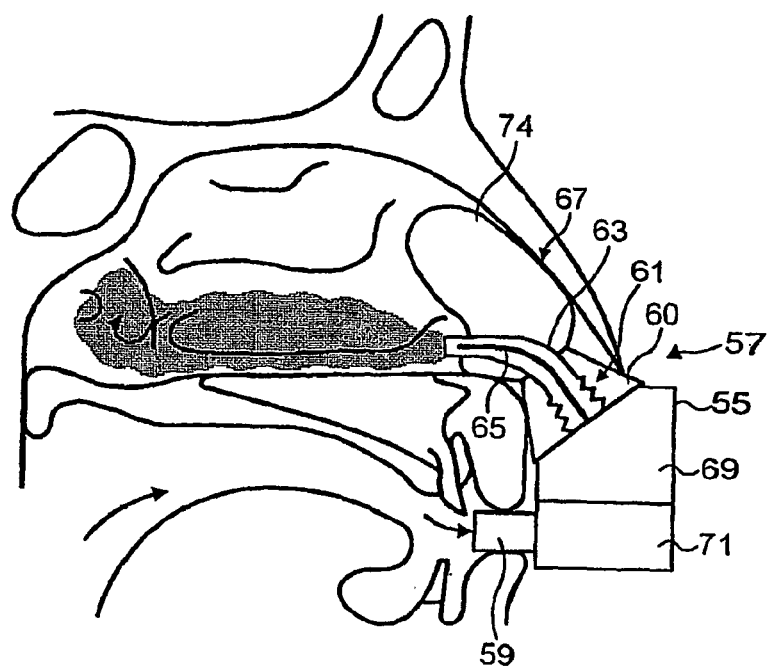
FIG. 25 schematically illustrates the delivery device of FIG. 23 during actuation.

Referring to FIG. 24, the nosepiece 57 is first inserted into one of the nasal cavities of a subject until the guide member 60 abuts the nares of the nostril, at which point the distal end of the outlet unit 61 extends about 2 cm into the nasal cavity of the subject, and the mouthpiece 59 is gripped in the lips of the subject.

The subject then begins to exhale through the mouthpiece 59, which exhalation acts to close the oropharyngeal velum of the subject and drive an air flow through the delivery channel 63 of the outlet unit 61, with the air flow passing into the one nasal cavity, around the posterior margin of the nasal septum and out of the other nasal cavity, thereby achieving a bi-directional air flow through the nasal airway of the subject. Exhalation through the mouthpiece 59 acts to develop a pressure in the delivery channel 63, which pressure acts to inflate the at least one cuff member 67. As illustrated in FIG. 25, the expansion of the at least one cuff member 67 acts to expand the nasal valve in the nasal cavity, seal the delivery channel 63 to the inner wall of the nasal cavity, and position the outlet unit 61 in relation to the nasal cavity of the subject. As will be noted from FIG. 25, the outlet unit 61 is forced to adopt the required position by the at least one cuff member 67, in this embodiment as accommodated by flexing of the outlet unit 61.

In this embodiment, when the flow rate developed through the delivery channel 63 reaches a predetermined value, the release mechanism 71 is triggered to actuate the substance supply unit 69 to deliver a metered dose of a substance to the nozzle 65 and into the nasal cavity of the subject. In the alternative embodiment the release mechanism 71 could be triggered on the generation of a predetermined pressure in the delivery channel 63.

Figure 26:
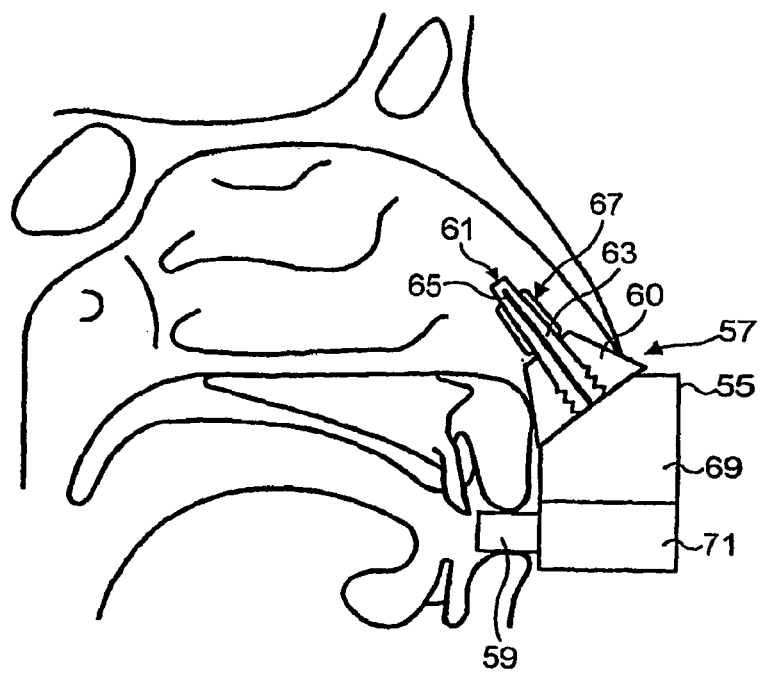
FIG. 26 schematically illustrates the delivery device of FIG. 23 following actuation.
Figure 27:
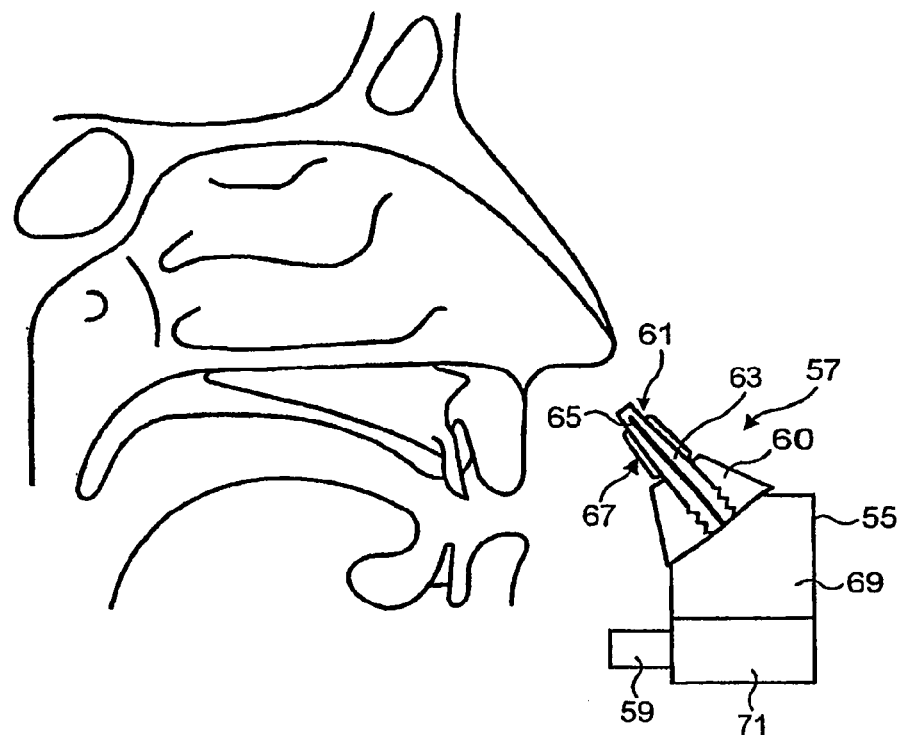
FIG. 27 schematically illustrates a nasal delivery device in accordance with an eighth embodiment of the present invention.
Figure 28:
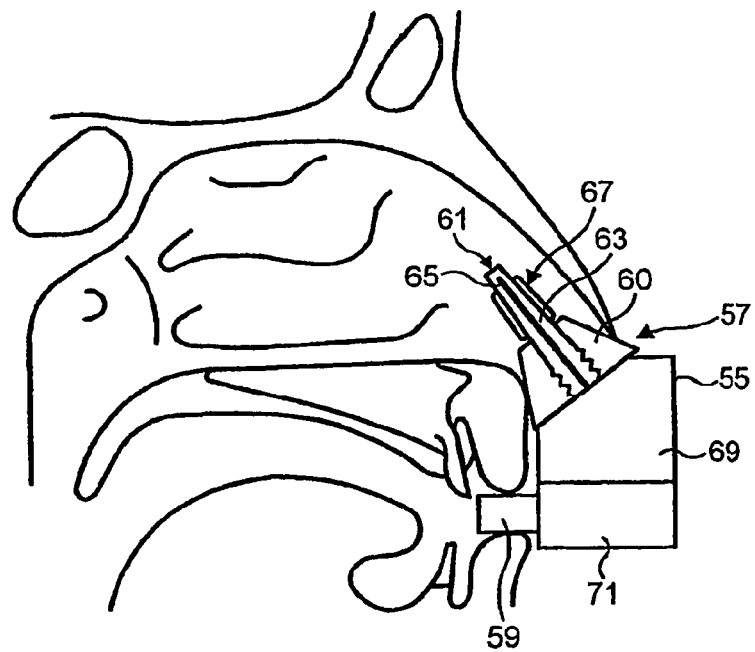
FIG. 28 schematically illustrates the delivery device of FIG. 27 inserted in a nasal cavity of a subject for operation.
Figure 29:
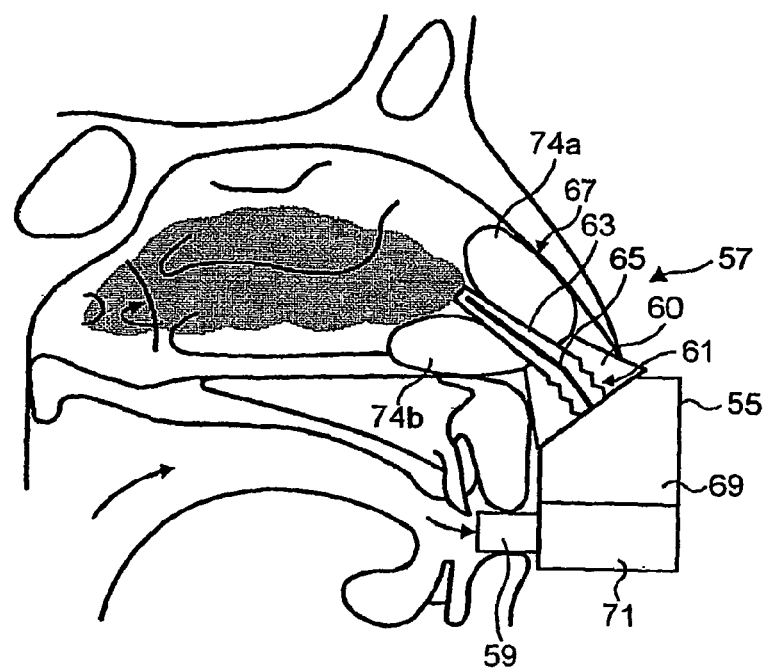
FIG. 29 schematically illustrates the delivery device of FIG. 27 during actuation.
Figure 30:
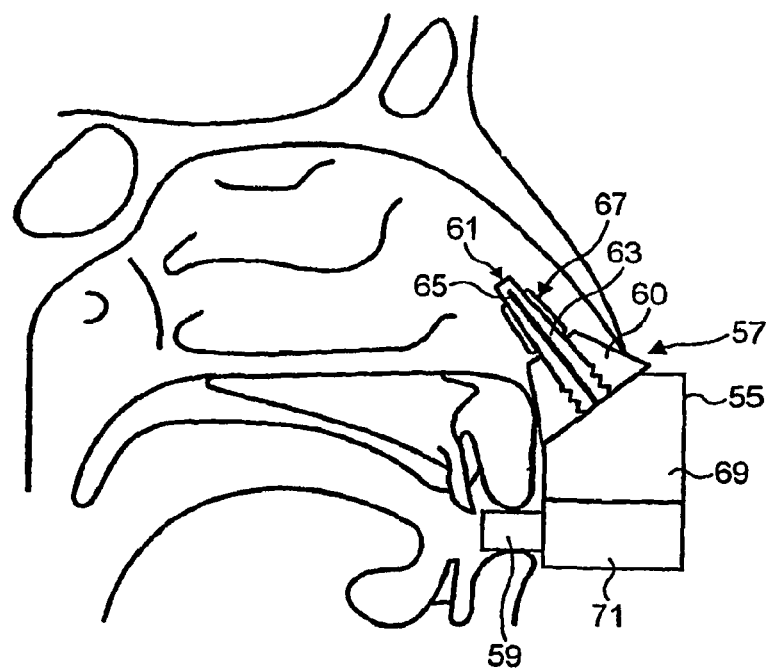
FIG. 30 schematically illustrates the delivery device of FIG. 27 following actuation.
Figure 31:
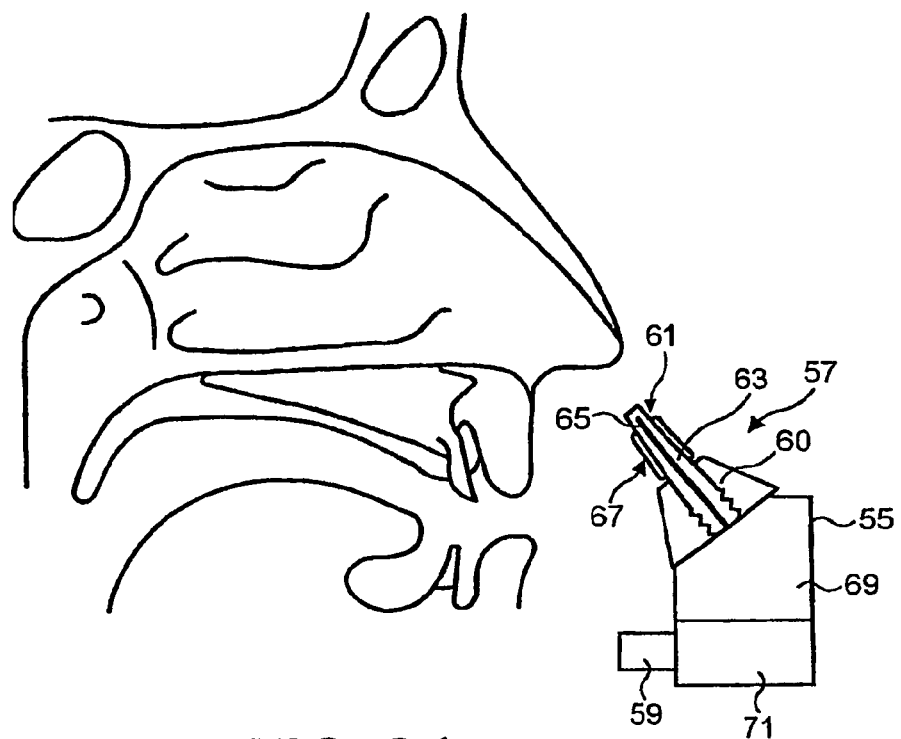
FIG. 31 schematically illustrates a nasal delivery device in accordance with a ninth embodiment of the present invention.
Figure 32:
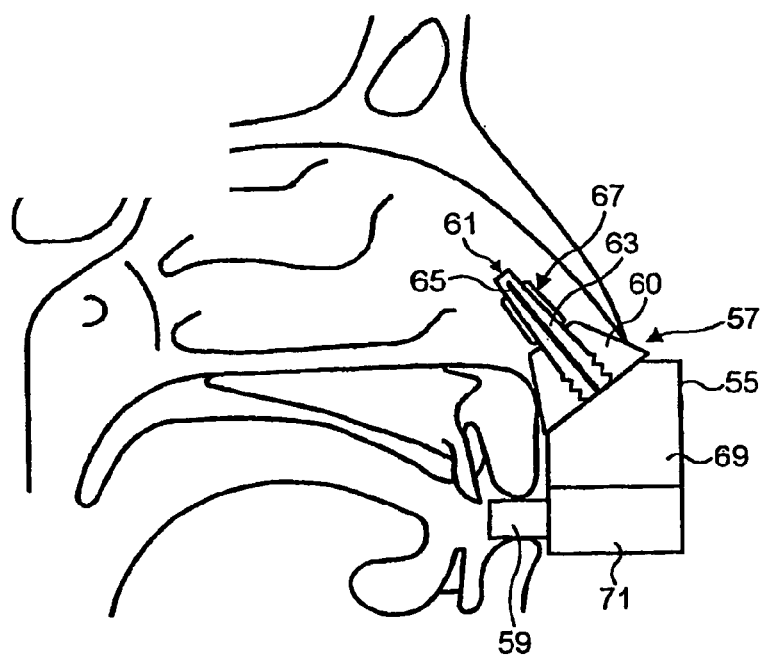
FIG. 32 schematically illustrates the delivery device of FIG. 31 inserted in a nasal cavity of a subject for operation.
Figure 33:
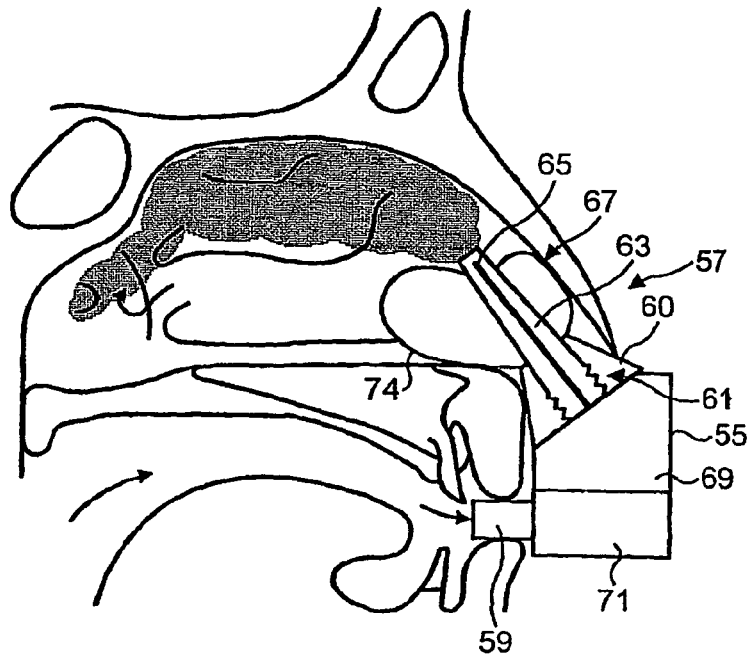
FIG. 33 schematically illustrates the delivery device of FIG. 31 during actuation.
Figure 34:
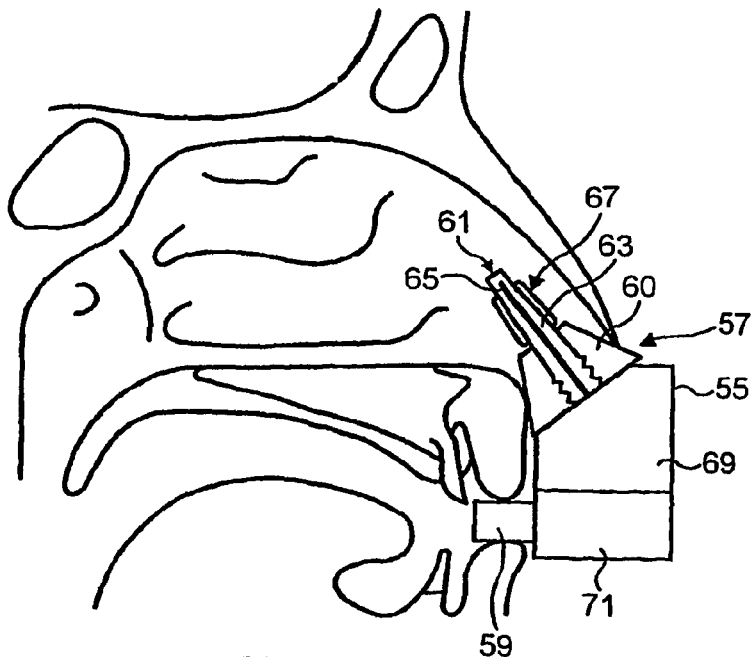
FIG. 34 schematically illustrates the delivery device of FIG. 31 following actuation.

Following exhalation, the pressure in the delivery channel 63 decreases and the at least one cuff member 67 deflates, as illustrated in FIG. 26, at which point the mouthpiece 59 is released and the nosepiece 57 withdrawn from the nasal cavity of the subject.

In one embodiment, where the delivery device is a single-dose device, the device can be discarded.

In another embodiment, where the delivery device is a multi-dose device, the device is ready for further use following priming of the substance supply unit 69. In a preferred embodiment, where the nosepiece 57 is replaceable, the nosepiece 57 can be replaced with a new nosepiece 57.

FIGS. 27 to 30 illustrate an exhalation breath-actuated nasal delivery device in accordance with an eighth embodiment of the present invention.

The delivery device of this embodiment is very similar to the delivery device of the above-described seventh embodiment, and thus, in order to avoid unnecessary duplication of description, only the differences will be described in detail, with like reference signs designating like parts.

The delivery device of this embodiment differs from that of the above-described seventh embodiment only in the configuration of the outlet unit 61 and the at least one cuff member 67.

In this embodiment the at least one cuff member 67 is configured such that, when inserted in the nasal cavity of the subject, the outlet unit 61 is directed at a middle region of the nasal cavity of the subject. In a preferred embodiment the at least one cuff member 67 can be configured to direct the outlet unit 61 at any region of the middle meatus and the inferior region of the superior meatus, whereby substance can be targeted in particular at the middle nasal concha, the sinus infundibulum and the sinus ostia.

The middle meatus is the region of the nasal cavity located under and lateral to the middle nasal concha, with the sinus infundibulum and the sinus ostia representing the sites of the main pathologies in many very common diseases, such as chronic sinusitis, which affects about 10 to 15% of the population and has no FDA approved treatment, and nasal polyposis. The only known treatment of these conditions is the application of drops during a rigorous and complex procedure involving severe neck extension and the so-called "Mecca" position. As will be appreciated, however, owing to the complicated and often painful procedure, compliance is very poor. Existing nasal spray systems are ineffective in delivering substance to this region of the nasal cavity.

In this embodiment the at least one cuff member 67 includes upper and lower lobes 74a, 74b which are configured such as to extend into, and thereby obstruct, respective ones of the upper and lower regions of the nasal cavity of the subject, the lobes 74a, 74b acting to force a delivered flow to follow a flow path defined by the middle meatus and the inferior region of the superior meatus. The achievement of such a flow path, allied with an optimization of the particle size distribution, provides that a much larger fraction of substance can be delivered to sites in the middle meatus and the inferior region of the middle meatus.

Operation of the delivery device is the same as for the above-described seventh embodiment.

FIGS. 31 to 34 illustrate an exhalation breath-actuated nasal delivery device in accordance with a ninth embodiment of the present invention.

The delivery device of this embodiment is very similar to the delivery device of the above-described seventh embodiment, and thus, in order to avoid unnecessary duplication of description, only the differences will be described in detail, with like reference signs designating like parts.

The delivery device of this embodiment differs from that of the above-described seventh embodiment only in the configuration of the outlet unit 61 and the at least one cuff member 67.

In this embodiment the at least one cuff member 67 is configured such that, when inserted in the nasal cavity of the subject, the outlet unit 61 is directed at a superior region of the nasal cavity of the subject. In a preferred embodiment the at least one cuff member 67 can be configured to direct the outlet unit 61 at any region of the superior meatus, and in particular provide for the targeting of the superior nasal concha and the olfactory region.

The olfactory region is located in the superior region of the nasal cavity and typically has a surface area of from about 4 to 6 $cm^2$. The olfactory region represents the only region where it is possible to circumvent the blood-to-brain barrier (BBB) and enable communication with the cerebrospinal fluid (CSF) and the brain. Such delivery is necessary to enable effective treatment of neurological diseases, such as Alzheimer's and Parkinson's disease, psychiatric diseases and intracerebral infections.

The olfactory region is reached through narrow slit-like passages and the delivery of substance to this region is not possible using existing nasal delivery systems.

In existing nasal spray systems, substantially all of the particles are far too large to pass through the passages in communication with the olfactory region. Indeed, such spray systems are specifically designed to deliver particles having an average diameter of greater than 10 µm in order to comply with the FDA requirements which require that the maximum fraction of particles having an average diameter of less than 10 µm be 5% of the total fraction. The reason for this requirement is that, where the velum is not closed, as would be the case where a subject inhales through the nose as prescribed for delivery, particles having an average diameter of less than 10 µm could escape from the nasal cavity and be inhaled into the lungs.

In addition, in existing nasal spray systems, the flow rate of particles delivered into the nasal cavity is too great to enable delivery through the passages communicating with the olfactory region.

Furthermore, inhalation by a subject during delivery causes the particles to be drawn into the inferior and middle regions of the nasal cavity, where the flow resistance is the lowest, with only a minimal fraction, if any, of the particles being delivered to the olfactory region.

In this embodiment, by ensuring closure of the velum in delivery and optimizing both the particle size distribution so as to include a larger fraction of smaller particles, typically having a particle size of less than 10 µm, and the aerodynamic delivery conditions, the delivery device provides for the effective delivery of substance to the olfactory region. Such a delivery regime has not previously been known, and has been recognised by the present applicant as providing an improved delivery device and delivery method.

In this embodiment the at least one lobe 74 of the at least one cuff member 67 is configured such as to extend into, and thereby obstruct, a lower region of the nasal cavity of the subject, the at least one lobe 74 acting to force a delivered flow to follow a flow path defined by the superior meatus and in particular the olfactory region. The achievement of such a flow path, allied with an optimization of the particle size distribution, provides that a much larger fraction of substance can be delivered to sites in the superior meatus and in particular the olfactory region.

Operation of the delivery device is the same as for the above-described seventh embodiment.

FIGS. 35 to 39 illustrate an exhalation breath-actuated nasal delivery device in accordance with a tenth embodiment of the present invention.

The delivery device comprises a housing 75, a nosepiece 77 for fitting in a nasal cavity of a subject, and a mouthpiece 79 through which the subject exhales to actuate the delivery device.

The nosepiece 77 comprises a cuff member 80, in this embodiment a frusto-conical element, for positioning the nosepiece 77 in the nasal cavity of the subject and providing a fluid-tight seal therewith, and an outlet unit 81 for delivering substance into the nasal airway of the subject.

In this embodiment the outlet unit 81 comprises a nozzle 82 from which substance is delivered into the nasal cavity of the subject, and a delivery channel 83 through which a gas flow, separate from the exhalation breath of the subject, is delivered to interact with the substance delivered from the nozzle 82. This configuration, in interacting with the substance and altering the characteristics of the delivered substance, advantageously provides for improved delivery of the substance.

In this embodiment the nozzle 82 is configured to provide an aerosol spray. In an alternative embodiment, for the delivery of a liquid, the nozzle 82 could be configured to deliver a liquid jet as a column of liquid.

In this embodiment the nozzle 82 is disposed in the delivery channel 83 co-axially with the same. In this embodiment the delivery channel 83 is an annular channel which surrounds the nozzle 82 such as to define an annular gas flow which interacts with the substance delivered from the nozzle 82.

The delivery device further comprises a substance supply unit 85 which is fluidly connected to the nozzle 82 such as to deliver a metered dose of a substance on actuation thereof. In this embodiment the substance supply unit 85 comprises a mechanical pump for delivering a metered dose of a substance on actuation thereof.

The delivery device further comprises a gas supply unit 87 which is fluidly connected to the delivery channel 83 for supplying a gas flow therethrough. The gas supply unit 87 comprises a cylinder 89, a piston 91 which is movably disposed within the cylinder 89 and defines a chamber 93 forward thereof which contains a gas, with a volume of the contained gas, typically about 5 ml, being expelled from the chamber 93 on actuation of the gas supply unit 87.

The delivery device further comprises a driving unit 95 which is actuatable to actuate the substance supply unit 85 and the gas supply unit 87.

Figure 37:
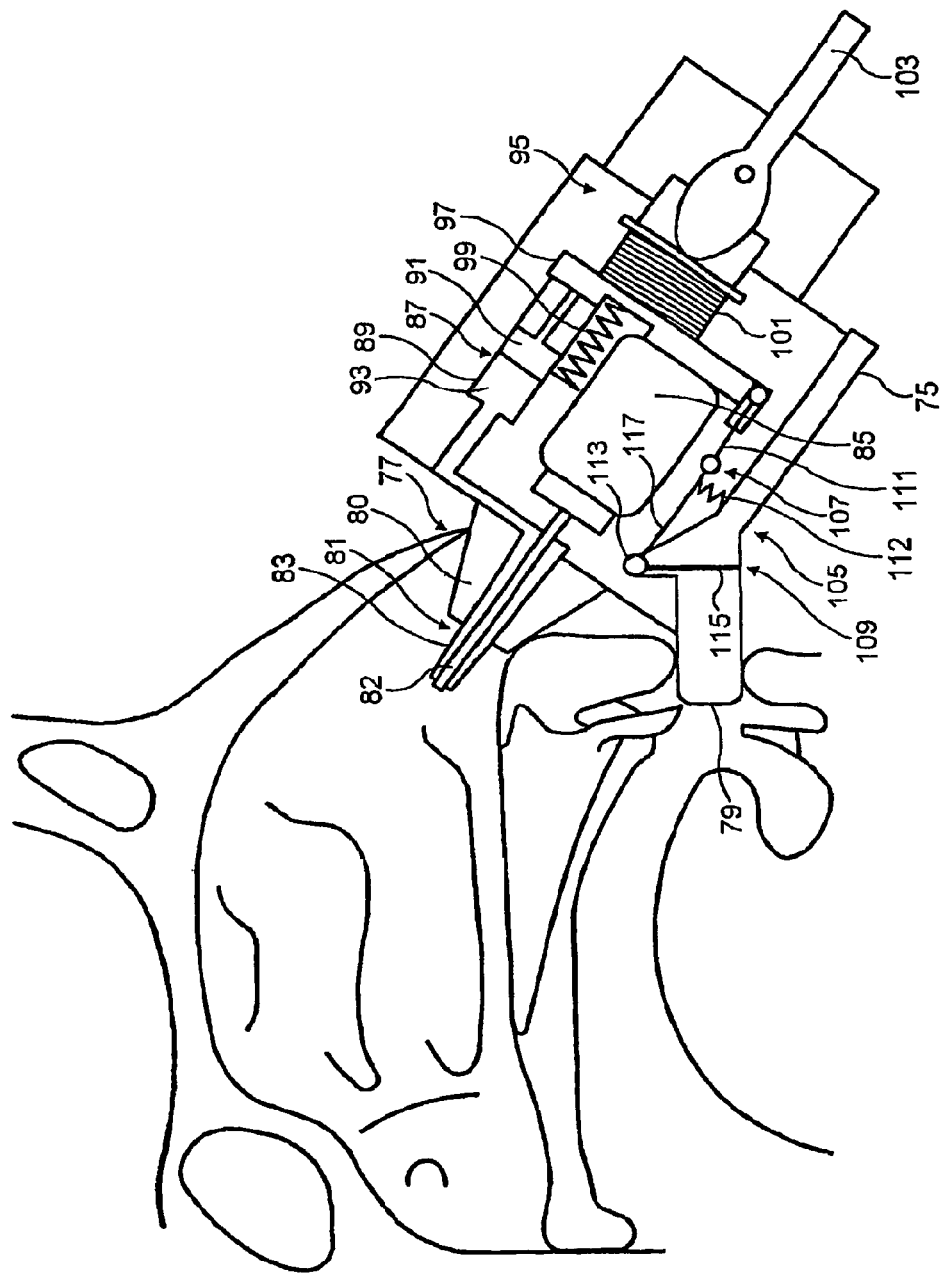
FIG. 37 schematically illustrates the delivery device of FIG. 35 inserted in a nasal cavity of a subject for operation.
Figure 38:
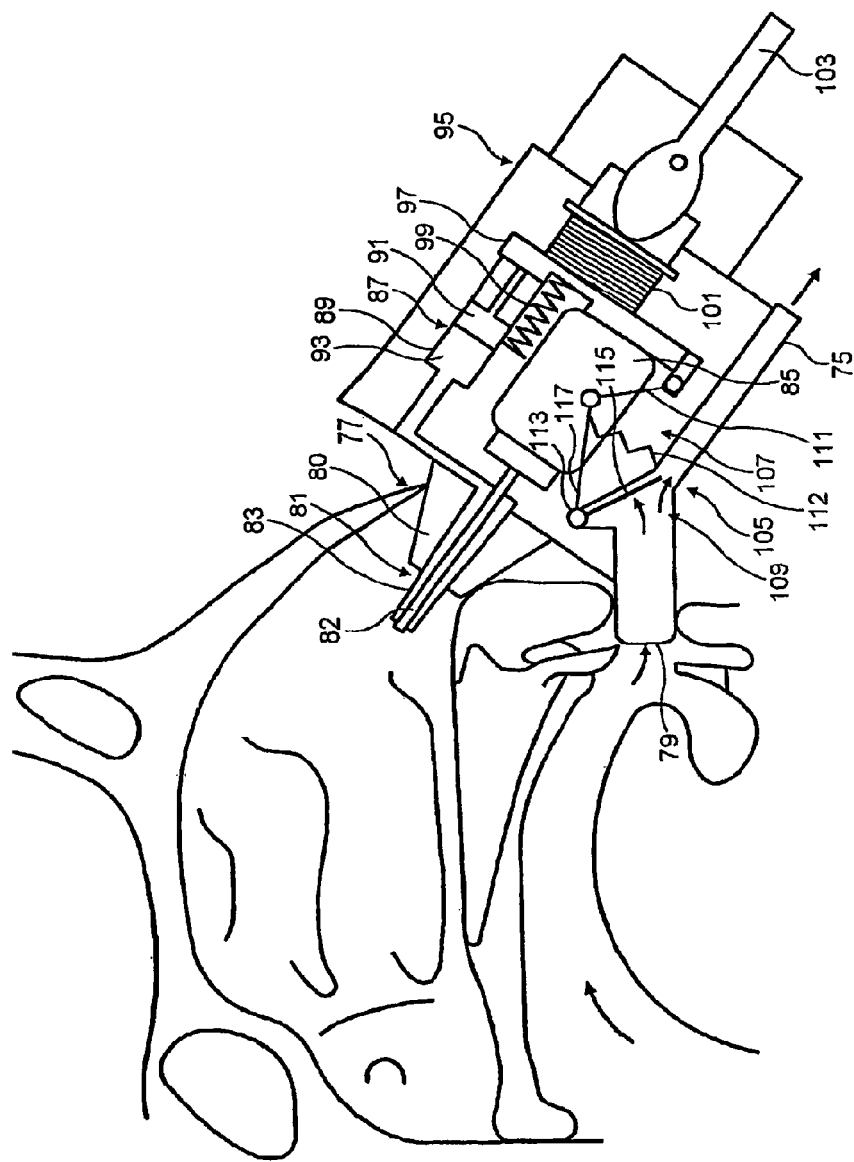
FIG. 38 schematically illustrates the delivery device of FIG. 35 during actuation where the subject has commenced exhaling and the delivery device is at the point of actuation.
Figure 39:
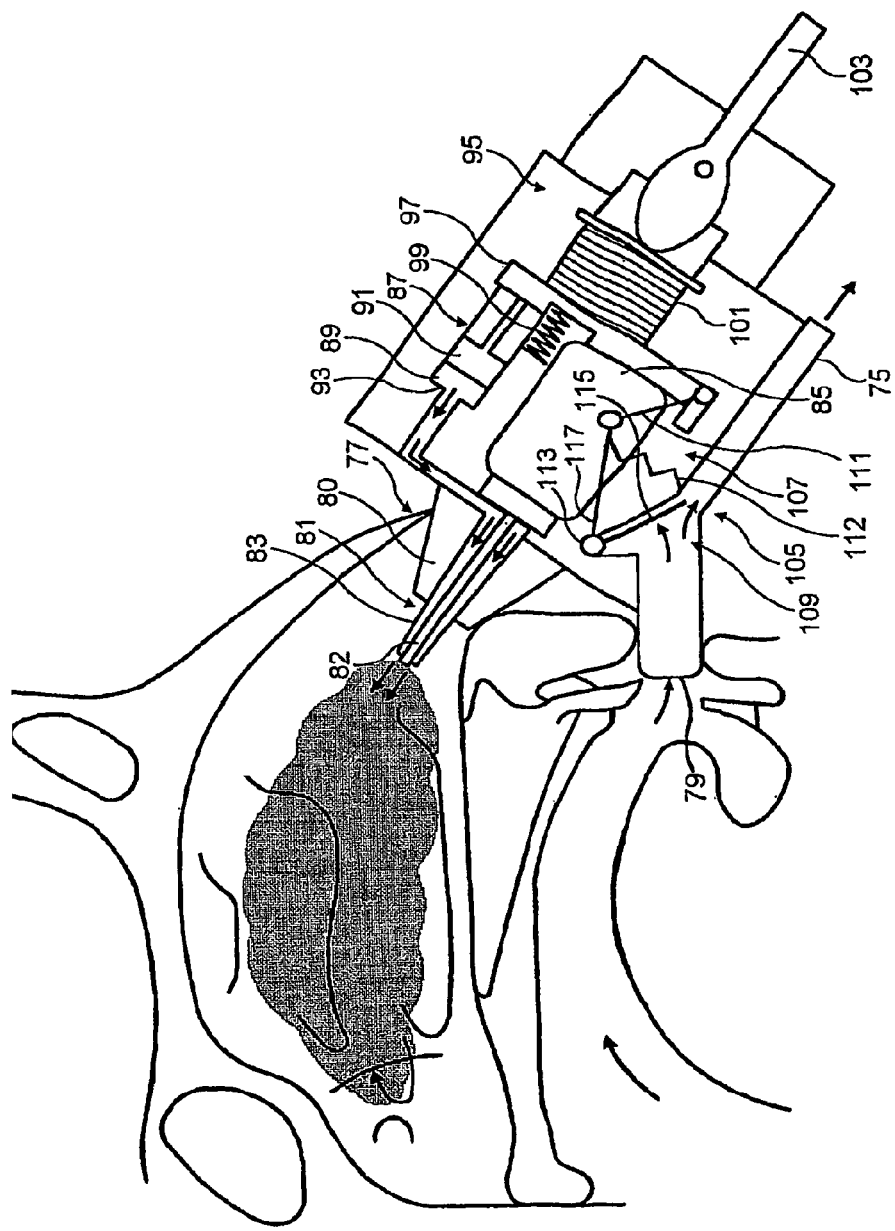
FIG. 39 schematically illustrates the delivery device of FIG. 35 during actuation.
Figure 40:
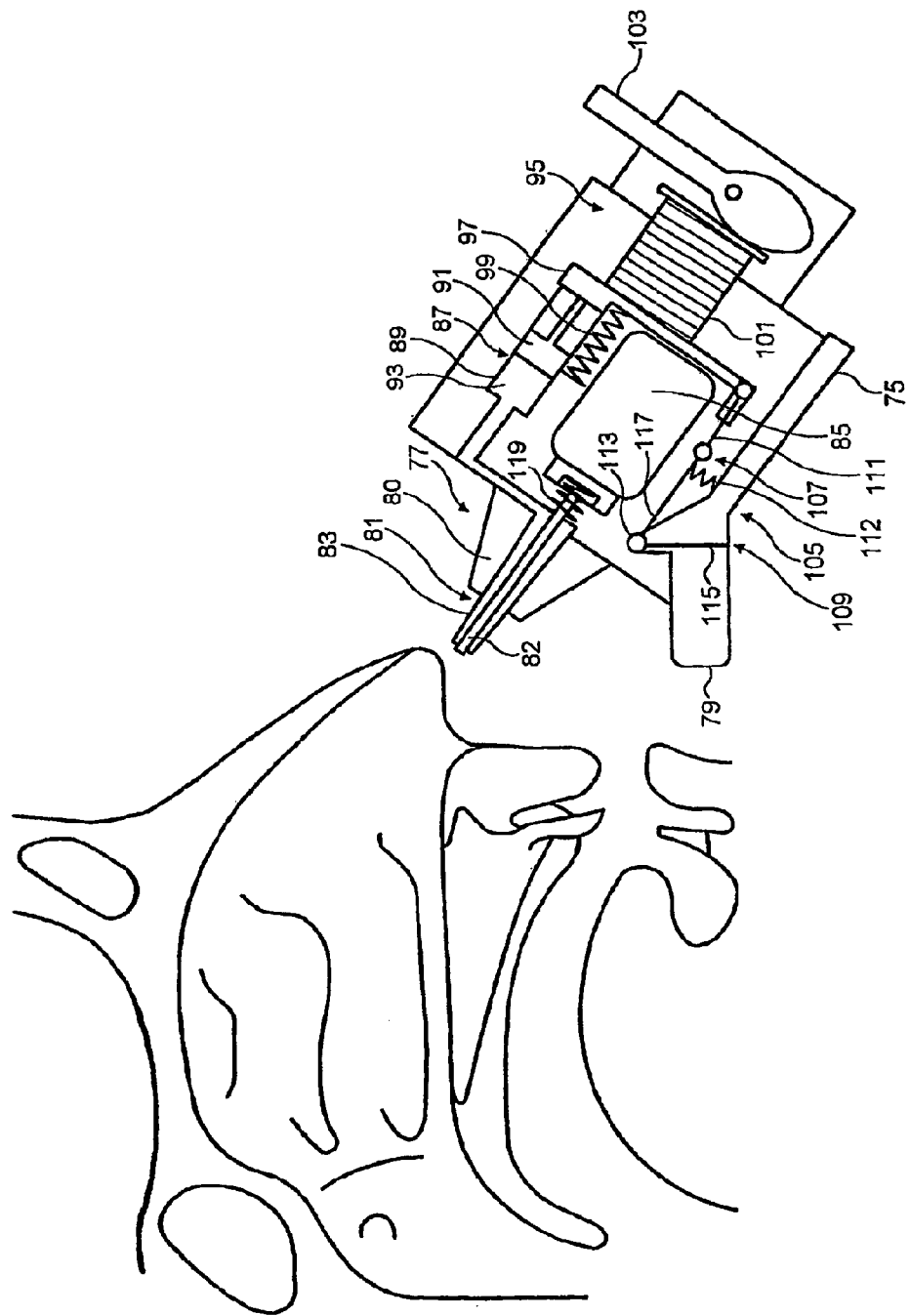
FIG. 40 schematically illustrates a nasal delivery device in accordance with an eleventh embodiment of the present invention, illustrated in the inoperative configuration.
Figure 41:
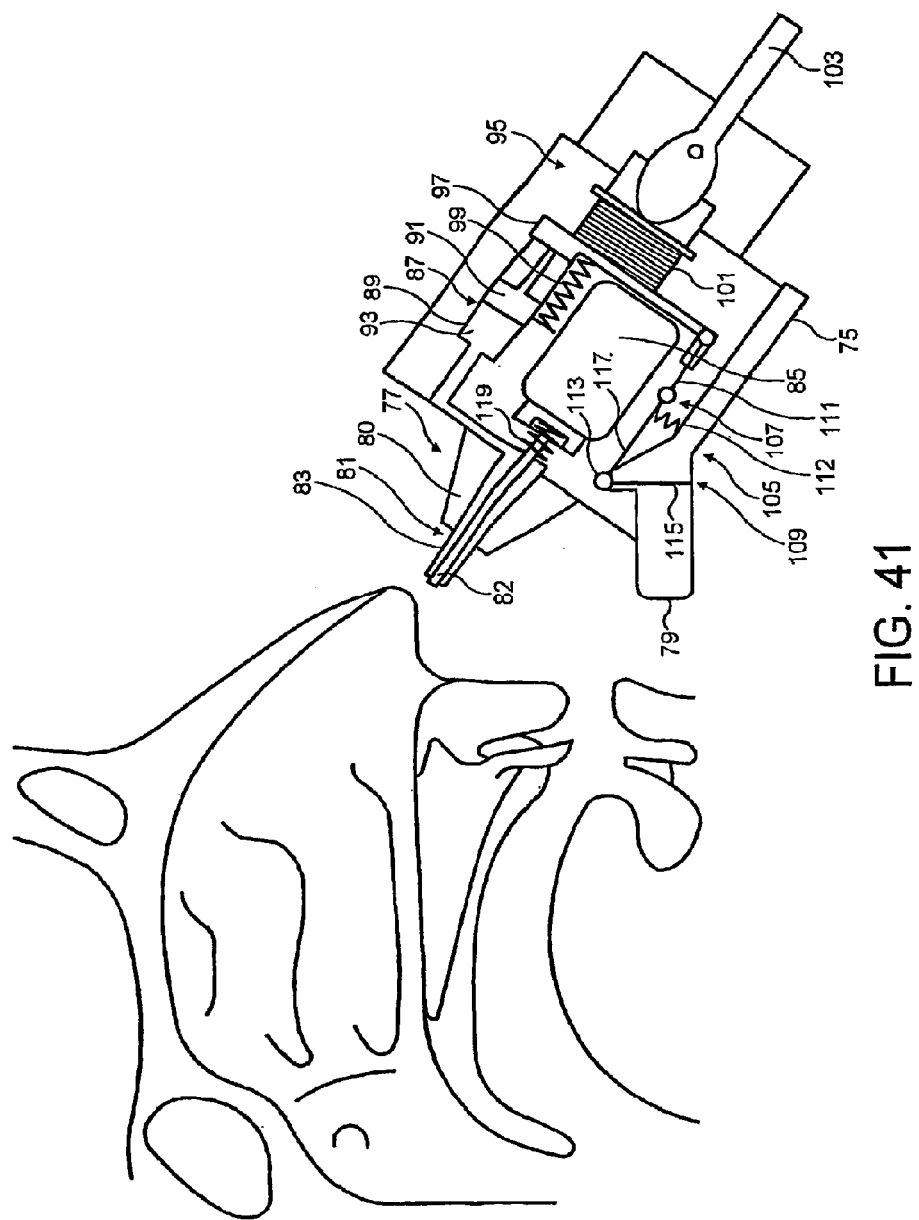
FIG. 41 schematically illustrates the delivery device of FIG. 40 where the driving unit is primed for actuation.
Figure 42:
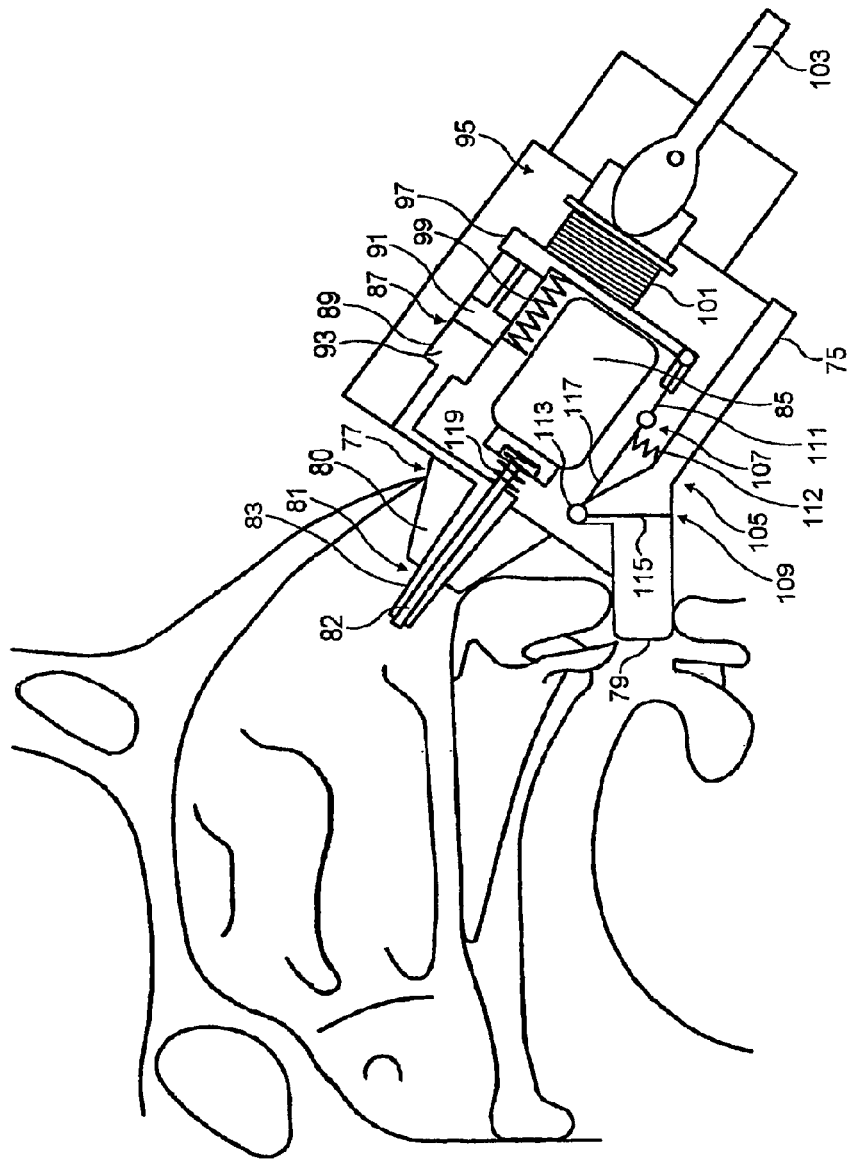
FIG. 42 schematically illustrates the delivery device of FIG. 40 inserted in a nasal cavity of a subject for operation.
Figure 43:
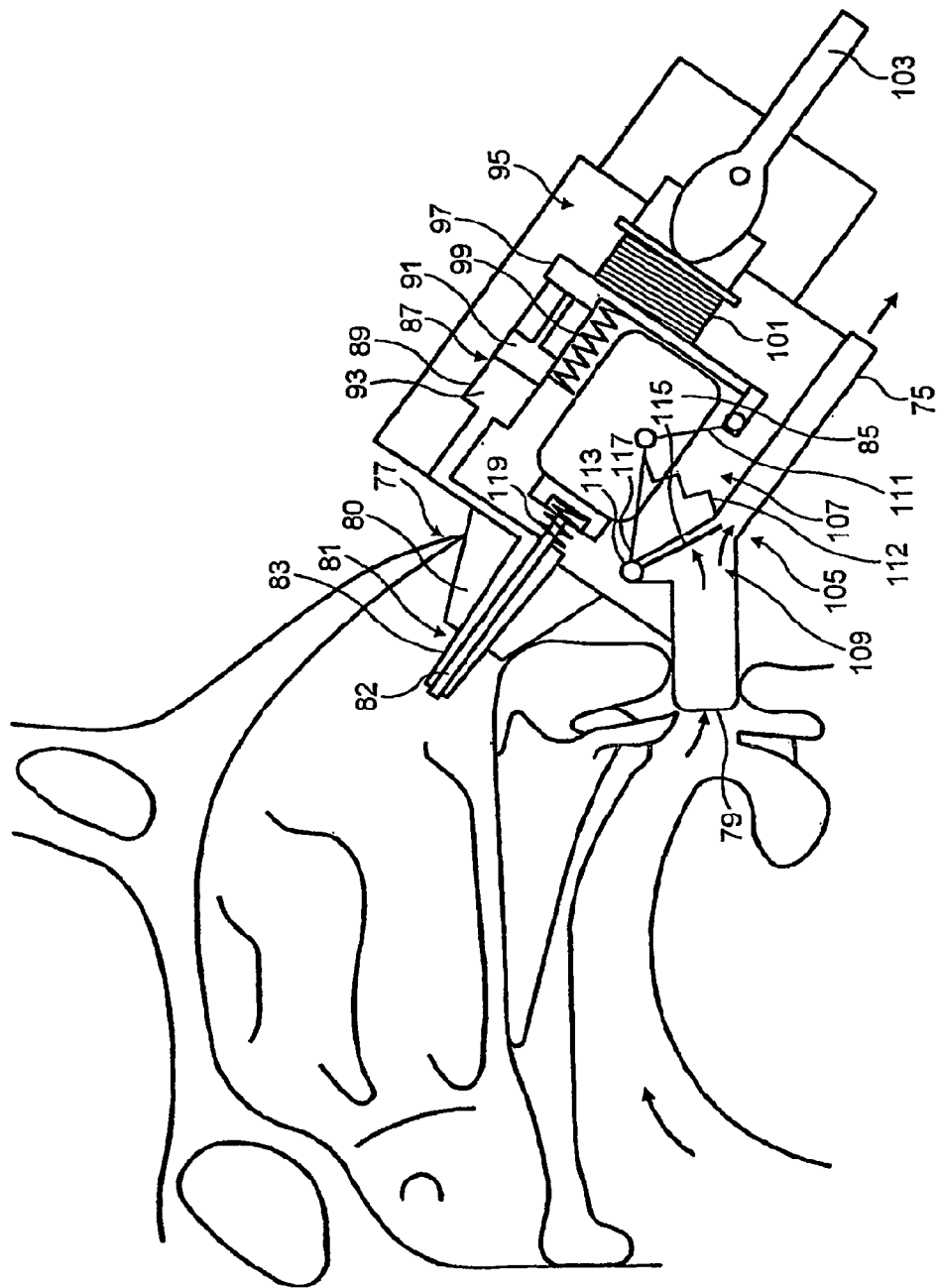
FIG. 43 schematically illustrates the delivery device of FIG. 40 where the subject has commenced exhaling and the delivery device is at the point of actuation.
Figure 44:
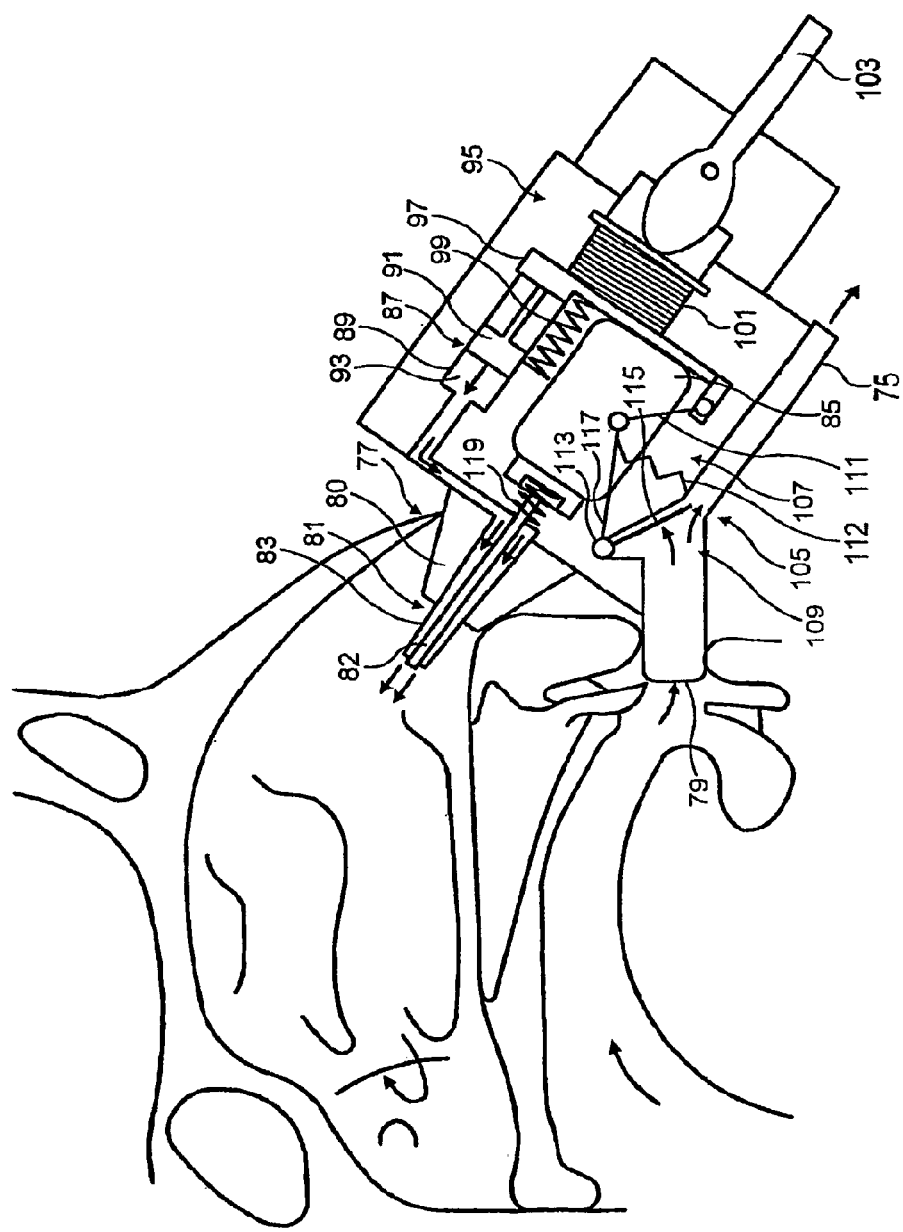
FIG. 44 schematically illustrates the delivery device of FIG. 40 where the driving unit has been actuated, the driving unit having initiated actuation of the gas delivery unit and being at the point of initiating actuation of the substance supply unit.
Figure 45:
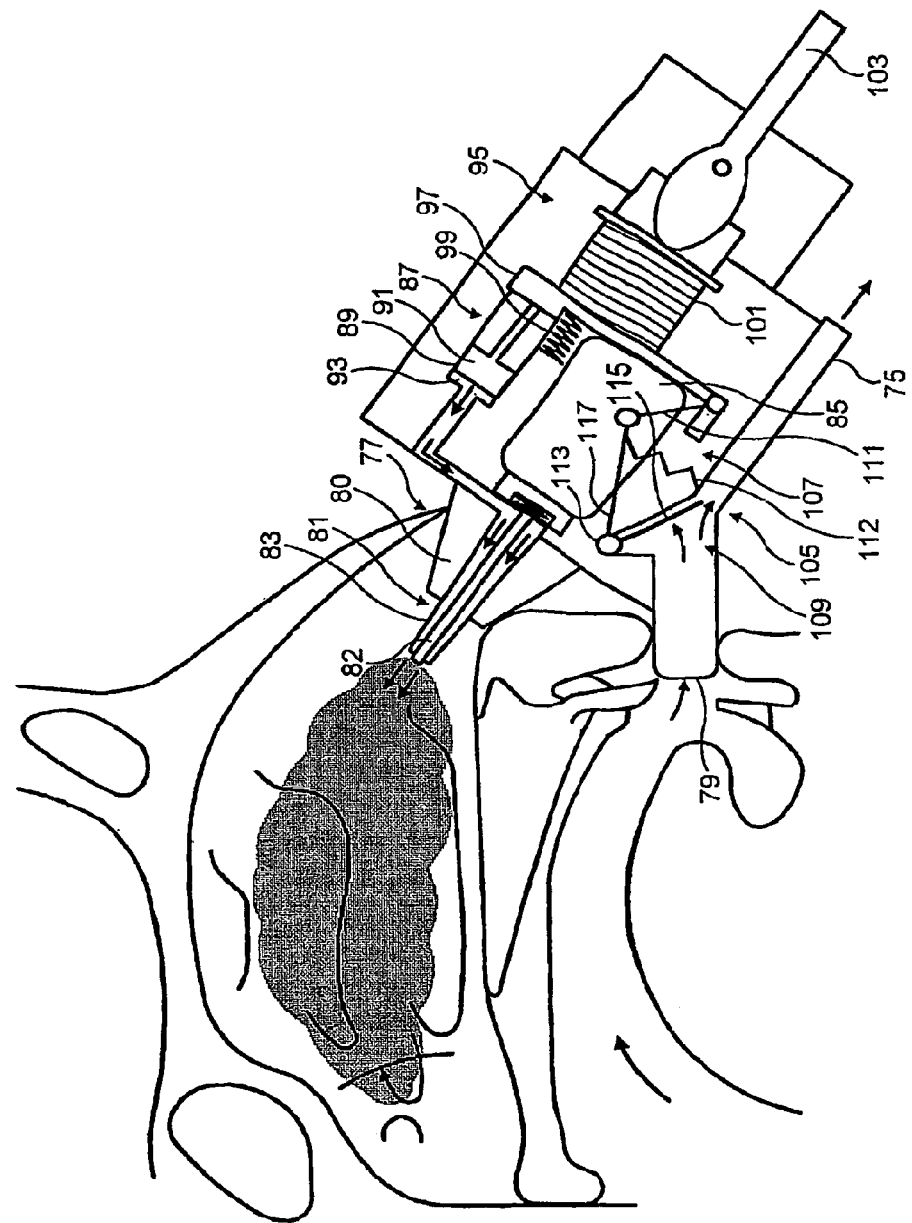
FIG. 45 schematically illustrates the delivery device of FIG. 40 during full actuation.
Figure 46:
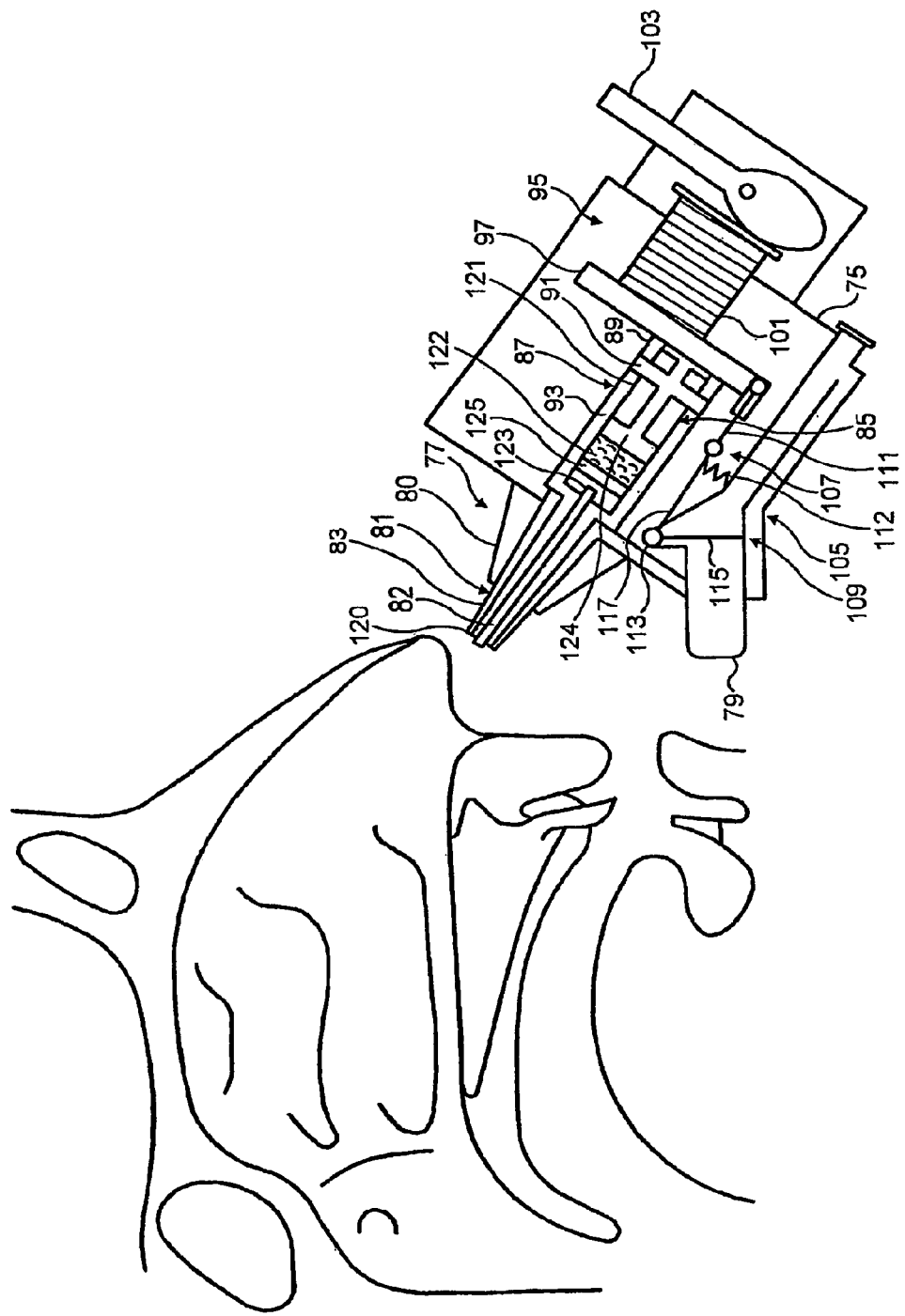
FIG. 46 schematically illustrates a nasal delivery device in accordance with a twelfth embodiment of the present invention, illustrated in the inoperative configuration.
Figure 47:
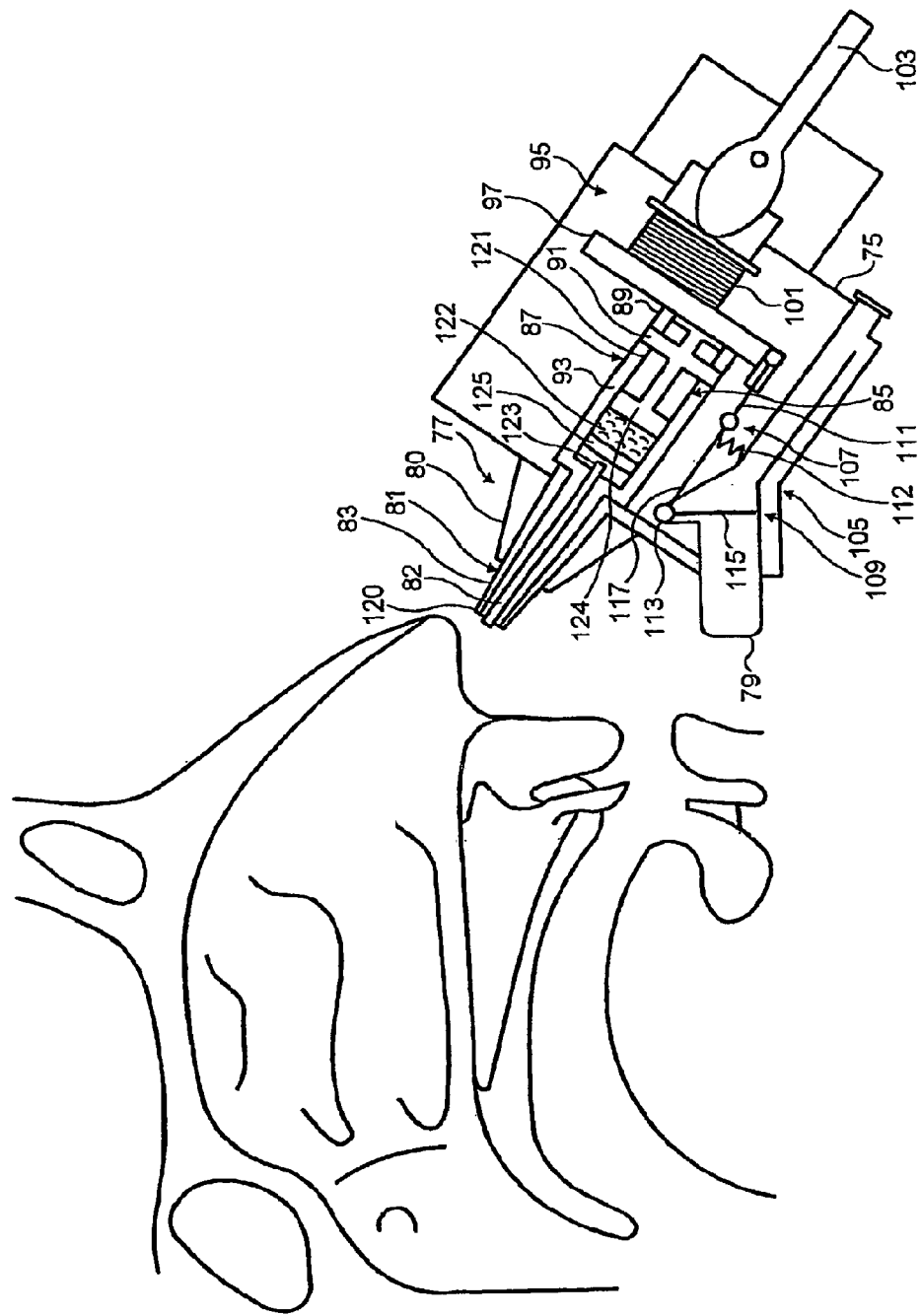
FIG. 47 schematically illustrates the delivery device of FIG. 46 where the driving unit is primed for actuation.
Figure 48:
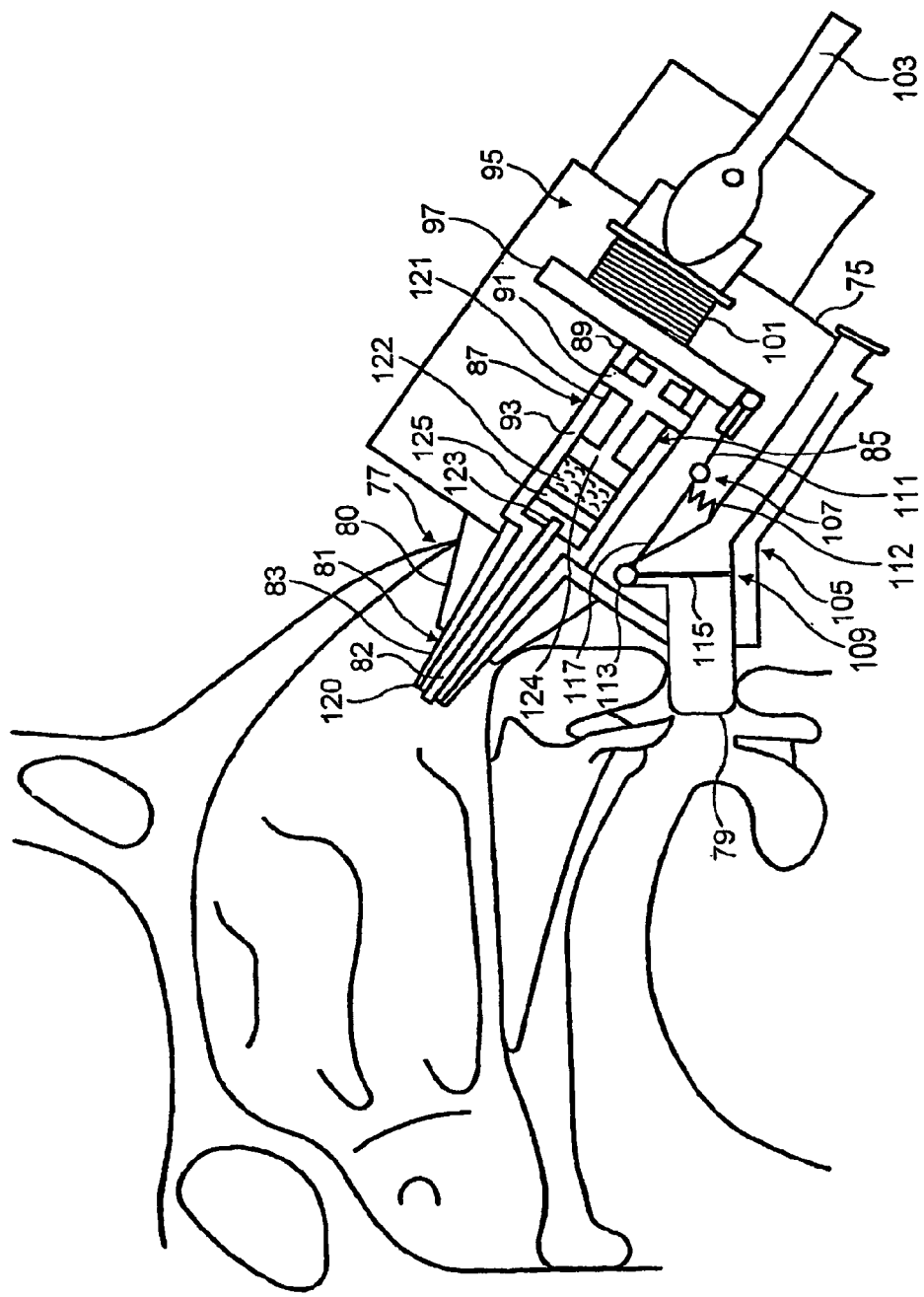
FIG. 48 schematically illustrates the delivery device of FIG. 46 inserted in a nasal cavity of a subject for operation.
Figure 49:
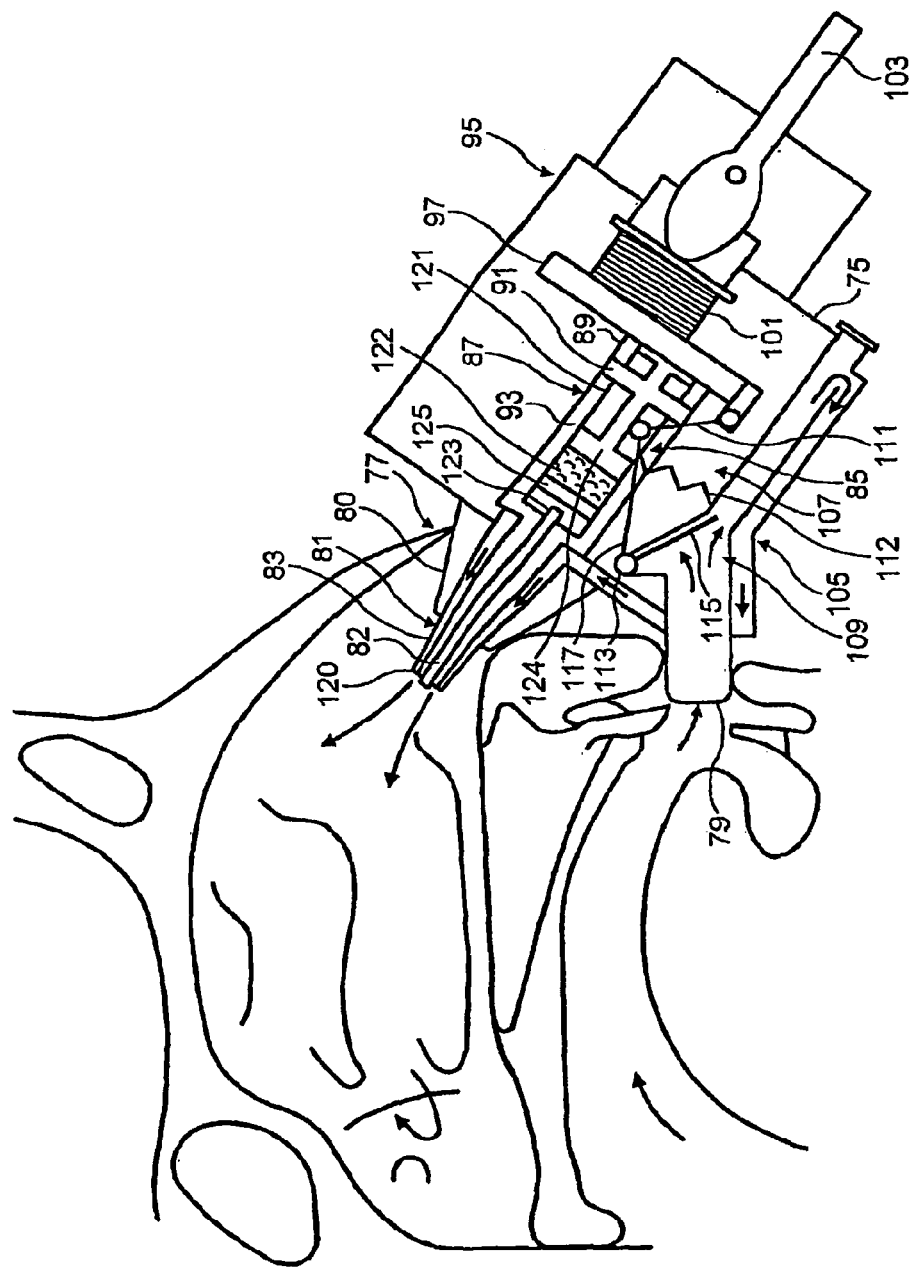
FIG. 49 schematically illustrates the delivery device of FIG. 46 where the subject has commenced exhaling and the delivery device is at the point of actuation.
Figure 50:
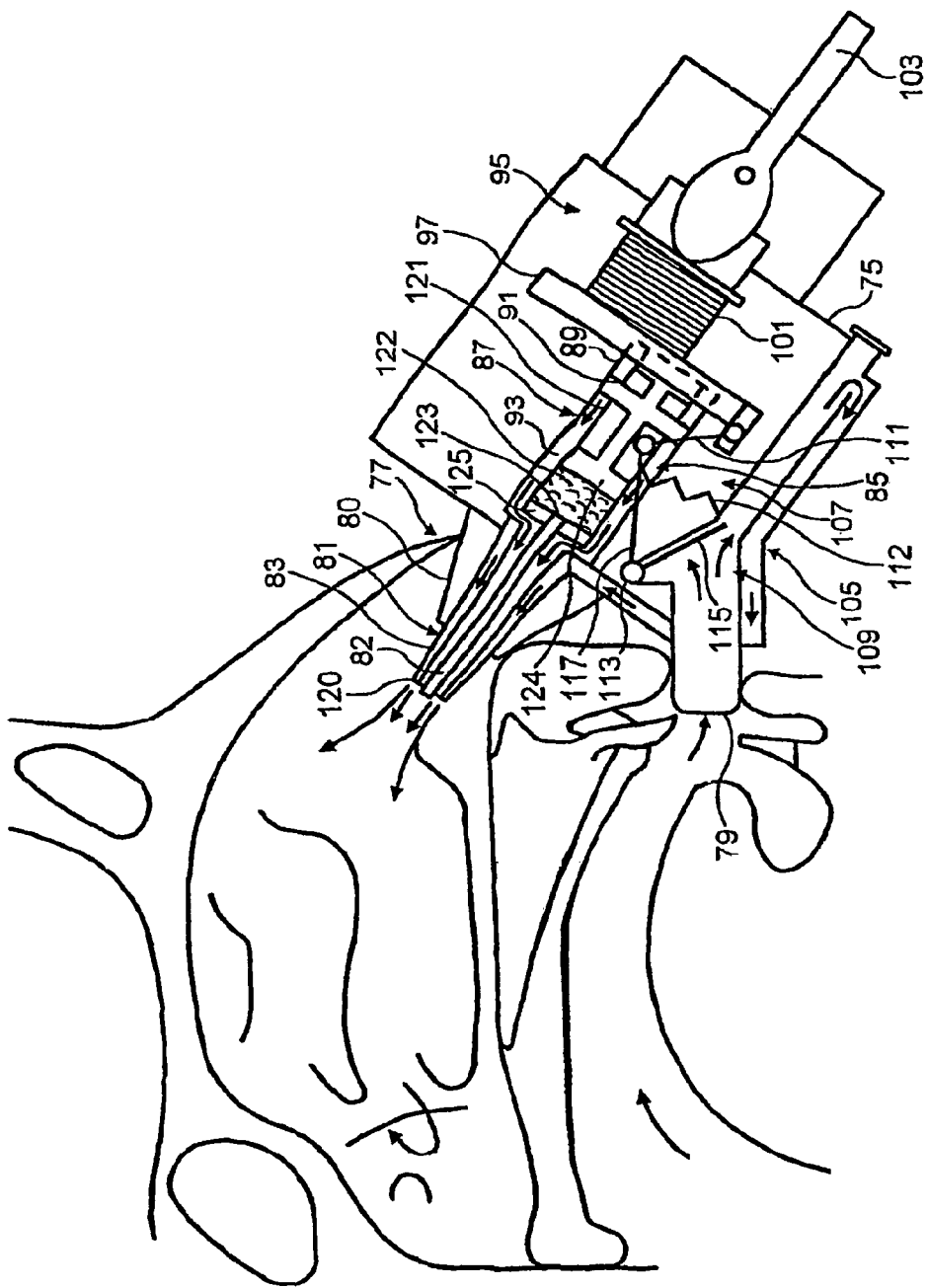
FIG. 50 schematically illustrates the delivery device of FIG. 46 where the driving unit has been actuated, the driving unit having initiated actuation of the gas delivery unit and being at the point of initiating actuation of the substance supply unit.
Figure 51:
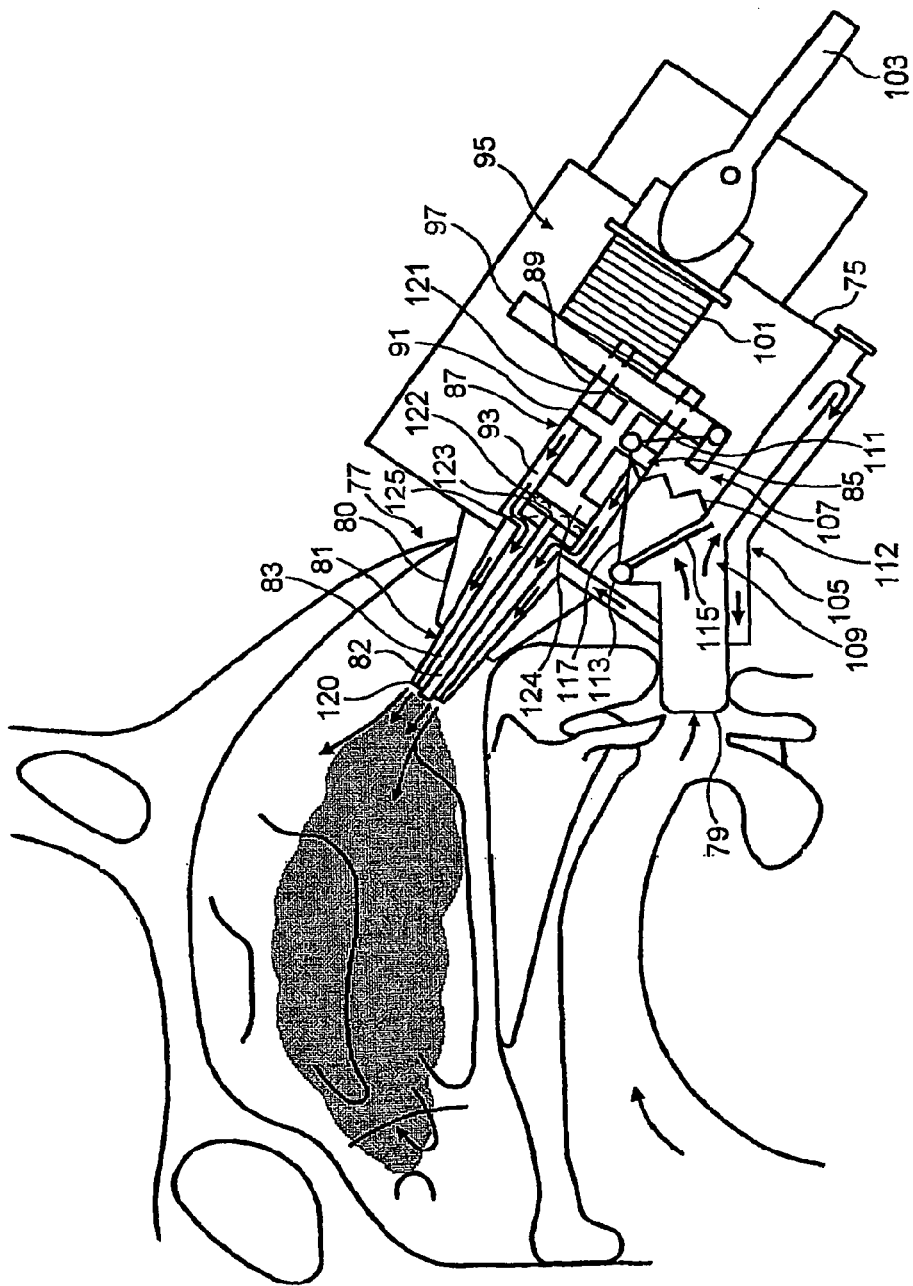
FIG. 51 schematically illustrates the delivery device of FIG. 46 during full actuation.

The driving unit 95 comprises a drive member 97, in this embodiment a block, which is coupled, here commonly coupled, to the body of the substance supply unit 85 and the piston 91 of the gas supply unit 87 and movable between a first, rest position (as illustrated in FIGS. 35 to 38) in which the substance supply unit 85 and the gas supply unit 87 are in the non-actuated positions and a second, actuated position (as illustrated in FIG. 39) in which the body of the substance supply unit 85 and the piston 91 of the gas supply unit 87 are advanced to the actuated positions, and a return biasing element 99, in this embodiment a resilient element, particularly a compression spring, for returning the drive member 97 to the rest position.

Figure 35:
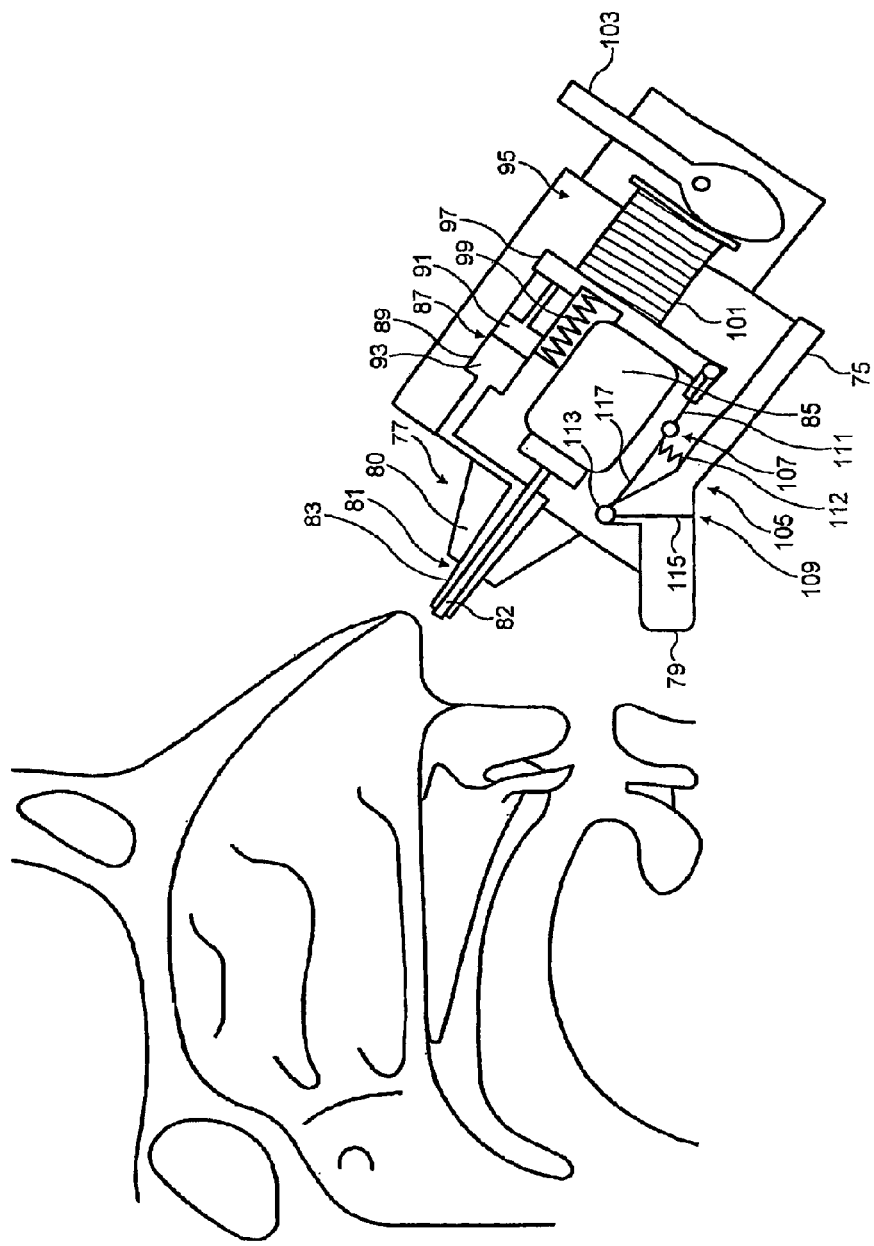
FIG. 35 schematically illustrates a nasal delivery device in accordance with a tenth embodiment of the present invention, illustrated in the inoperative configuration.
Figure 36:
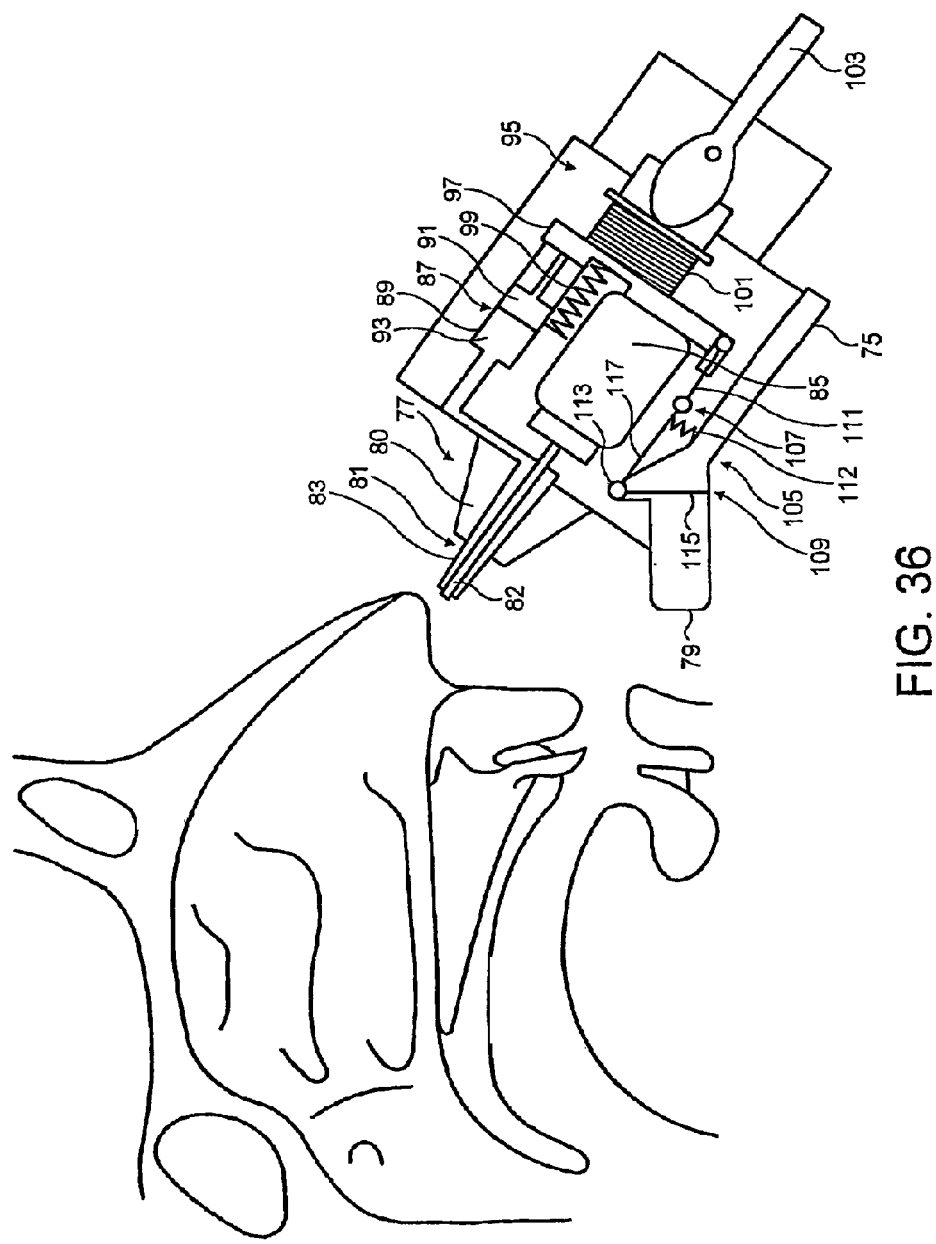
FIG. 36 schematically illustrates the delivery device of FIG. 35 where the driving unit is primed for actuation.

The driving unit 95 further comprises a load biasing element 101, in this embodiment a resilient element, particularly a compression spring, for biasing the drive member 97 in an actuating direction when in the rest position, and a loading member 103, in this embodiment a lever, for loading the load biasing element 101 such as to bias the drive member 97 when in the rest position with an actuation force. The loading member 103 is movable between a first, inoperative position (as illustrated in FIG. 35) in which the load biasing element 101 is not loaded thereby, and a second, operative position (as illustrated in FIGS. 36 to 38) in which the biasing element 101, when restrained, loads the drive member 97 with the actuation force.

The delivery device further comprises a trigger mechanism 105 which is configured normally to lock the drive member 97 of the driving unit 95 in the rest position and release the same on exhalation by the subject through the mouthpiece 79, which drive member 97, when loaded by the load biasing element 101, once released acts commonly to actuate the substance supply unit 85 and the gas supply unit 87.

In this embodiment the trigger mechanism 105 is configured to cause actuation of the driving unit 95 on generation of a predetermined flow rate through the mouthpiece 79.

In another embodiment the trigger mechanism 105 could be configured to cause actuation of the driving unit 95 on generation of a predetermined pressure within the mouthpiece 79.

In this embodiment the trigger mechanism 105 comprises a linkage assembly 107 which includes first and second link elements 109, 111, and a biasing element 112, in this embodiment a resilient element, particularly a tension spring, for biasing the linkage assembly 107 to a locking configuration (as illustrated in FIGS. 35 to 37) in which the linkage assembly 107 acts to lock the drive member 97 of the driving unit 95 in the rest position and prevent movement thereof when loaded by the load biasing element 101.

One of the link elements 109 includes a pivot 113 about which the same is rotatable, and first and second arms 115, 117. One of the arms 115 extends into the mouthpiece 79 and, when the linkage assembly 107 is in the locking configuration, is biased to a rest position (as illustrated in FIGS. 35 to 37) in which the flow path through the mouthpiece 79 is substantially closed, the one arm 115 thereby providing a vane to be acted upon by the exhalation breath of the subject.

The other of the link elements 111 is pivotally coupled at one end to the distal end of the other, second arm 117 of the first link element 109 and at the other end to the drive member 97 of the driving unit 95; the second arm 117 of the first link element 109 being angularly positioned relative to the first arm 115 thereof such that, when the linkage assembly 107 is in the locking configuration, the second arm 117 of the first link element 109 and the second link element 111 enclose an angle of less than 180 degrees on the side opposite to the first arm 115 of the first link element 109, whereby the second arm 117 of the first link element 109 and the second link element 111 are over-centered and support the drive member 97 of the driving unit 95 when loaded.

Operation of the delivery device will now be described hereinbelow with reference to FIGS. 36 to 39 of the accompanying drawings.

In a first step, as illustrated in FIG. 36, the loading member 103 is operated to bias the biasing element 101 and load the drive member 97 of the driving unit 95 with the actuation force.

Referring to FIG. 37, the nosepiece 77 is then first inserted into a nasal cavity of a subject until the cuff member 80 is fitted in the nares of the nostril, at which point the distal end of the outlet unit 81 extends about 2 cm into the nasal cavity of the subject, and the mouthpiece 79 is gripped in the lips of the subject.

The subject then begins to exhale through the mouthpiece 79, which exhalation acts to close the oropharyngeal velum of the subject and drive an air flow over the first arm 115 of the first link element 109 of the linkage assembly 107 which extends into the mouthpiece 79. While the flow rate developed is not sufficient to actuate the trigger mechanism 105, the linkage assembly 107 of the trigger mechanism 105 acts to retain the drive member 97 of the driving unit 95 in the locked position, whereby the substance supply unit 85 and the gas supply unit 87 are not actuated. When the flow rate developed reaches a predetermined value, as illustrated in FIG. 38, the rotation of the first arm 115 of the first link element 109 is such as to rotate the second atm 117 of the first link element 109 to a position in which the support provided together with the second link element 111 is unstable and collapses. Referring to FIG. 39, this collapse of the linkage assembly 107 enables the drive member 97 of the driving unit 95 to be moved by the load biasing element 101 to the actuated position, which movement actuates the substance supply unit 85 to deliver a metered dose of a substance through the nozzle 82 and the gas supply unit 87 to deliver a metered volume of a gas through the delivery channel 83, which gas flow interacts with the delivered substance to modify the characteristics of the delivered substance, and thereby provide for improved delivery to the nasal airway of the subject.

Following actuation, the mouthpiece 79 is released and the nosepiece 77 is withdrawn from the nasal cavity of the subject.

The loading member 103 of the driving unit 95 is then returned to the inoperative position, and the drive member 97 of the driving unit 95 is returned to the rest position by the return biasing element 99. The return of the drive member 97 to the rest position causes the body of the substance supply unit 85 and the piston 91 of the gas supply unit 87 to be returned to the rest positions.

Following the return of the drive member 97 to the rest position, the linkage assembly 107 again adopts the locking configuration, with the linkage assembly 107 being maintained in the locking configuration by the linkage biasing element 112. In this configuration, the delivery device is ready for further use.

FIGS. 40 to 45 illustrate an exhalation breath-actuated nasal delivery device in accordance with an eleventh embodiment of the present invention.

The delivery device of this embodiment is very similar to the delivery device of the above-described tenth embodiment, and thus, in order to avoid unnecessary duplication of description, only the differences will be described in detail, with like reference signs designating like parts.

The delivery device of this embodiment differs from that of the above-described tenth embodiment only in the configuration of the driving unit 95.

In this embodiment the drive member 97 of the drive unit 95 is not configured to commence actuation of the substance supply unit 85 and the gas supply unit 87 at the same instant as in the above-described tenth embodiment, but rather is configured such that actuation of the gas supply unit 87 is commenced prior to the actuation of the substance supply unit 85, whereby an interacting gas flow is delivered from the delivery channel 83 of the outlet unit 81 prior to the delivery of substance from the nozzle 82 and then during the delivery of substance from the nozzle 82 such as to interact with the same.

In this embodiment the delayed actuation of the substance supply unit 85 is achieved by configuring the drive member 97 such as to be spaced from the body of the substance supply unit 85 when the drive member 97 is in the rest position, whereby the drive member 97 has to be advanced a predetermined distance, corresponding to a predetermined time period, prior to common actuation of the substance supply unit 85 and the gas supply unit 87. In this embodiment the substance supply unit 85 includes a biasing element 119 for returning the substance supply unit 85 to the rest position following actuation. With this configuration, the interval between actuation of the gas supply unit 87 and the common actuation of the substance supply unit 85 and the gas supply unit 87 can be controlled by altering the spacing between the drive member 97 and the body of the substance supply unit 85.

Operation of the delivery device is the same as for the above-described tenth embodiment.

FIGS. 46 to 51 illustrate an exhalation breath-actuated nasal delivery device in accordance with a twelfth embodiment of the present invention.

The delivery device of this embodiment is very similar to the delivery device of the above-described tenth embodiment, and thus, in order to avoid unnecessary duplication of description, only the differences will be described in detail, with like reference signs designating like parts.

The delivery device of this embodiment differs from that of the above-described tenth embodiment only in the configuration of the outlet unit 81 and in the integration of the substance supply unit 85 and the gas delivery unit 87.

In this embodiment the outlet unit 81 includes a second delivery channel 120, here an annular channel which is disposed co-axially about the nozzle 82, through which an air flow from an exhalation breath of a subject is delivered, such as to entrain with the substance delivered from the nozzle 82. In this embodiment the second delivery channel 120 is fluidly connected to the mouthpiece 79 downstream of the trigger mechanism, and the mouthpiece 79 includes a pressure-release valve which allows for the development of a flow above the release pressure of the pressure-release valve where a flow, or at least not a sufficient flow, cannot be developed through the nasal airway of the subject.

In this embodiment the substance supply unit 85 comprises a piston unit which is disposed within the chamber 93 of the gas supply unit 87. The substance supply unit 85 comprises a cylinder 121 which defines a chamber 122 and into one, forward end of which a hollow needle 123 extends as an extension of the nozzle 82. The substance supply unit 85 further comprises first and second pistons 124, 125 which contain a volume of substance therebetween and are movably disposed within the chamber 122.

With this configuration, the forward, piston 125 is driven forwardly on the rear, piston 124 being driven forwardly, the substance contained between the pistons 124, 125 being substantially incompressible. The forward piston 125 is a puncturable member which is punctured by the needle 123 of the nozzle 82 on being driven onto the same, with the needle 123 of the nozzle 82 being in fluid communication with the substance contained between the pistons 124, 125 on puncturing the forward piston 125.

In this embodiment the forward piston 125 of the substance supply unit 85 is spaced from the needle 123 of the nozzle 82 by a predetermined distance such that the piston 91 of the gas supply unit 87, which drives the rear piston 124 of the substance supply unit 85, is required to be driven a predetermined distance before the forward piston 125 of the substance supply unit 85 is ruptured and substance is delivered through the nozzle 82. In this way, actuation of the gas supply unit 87 is initiated prior to the actuation of the substance supply unit 85, whereby an interacting gas flow is delivered from the delivery channel 83 of the outlet unit 81 prior to the delivery of substance from the nozzle 82 and then during the delivery of substance from the nozzle 82 such as to interact with the same. In this embodiment the interval between actuation of the gas supply unit 87 and the common actuation of the substance supply unit 85 and the gas supply unit 87 can be controlled by altering the spacing between the forward piston 125 of the substance supply unit 85 and the needle 123 of the nozzle 82.

Operation of the delivery device is the same as for the above-described tenth embodiment.

Finally, it will be understood that the present invention has been described in its preferred embodiments and can be modified in many different ways without departing from the scope of the invention as defined by the appended claims.

In particular, it should be understood that features of any of the embodiments could be incorporated in any other of the embodiments. For example, the second and third embodiments could incorporate features of the first embodiment, in particular the at least one expandable cuff member 23 as in the first embodiment.

Also, in embodiments where an entraining gas flow is not required through the nasal airways of subjects, ones of the embodiments could be modified to include no such gas flow. For example, the first-described embodiment could be modified such that the outlet unit 21 includes only the nozzle 23 and no delivery channel 23.

In the described embodiments the mouthpieces are configured to be gripped in the lips of a subject. In alternative embodiments the mouthpieces could be configured to be gripped by the teeth of a subject and sealed by the lips of the subject. In preferred embodiments the mouthpieces could be specifically configured to have one or both of a shape or geometry which allows the delivery devices to be gripped repeatedly in the same position, thereby providing for the respective nosepieces to be reliably inserted in the same position in the nasal cavity.

In preferred embodiments the delivery devices are configured to deliver substance through one nostril of a subject at such a pressure as to flow around the posterior margin of the nasal septum and out of the other nostril of the subject, thereby achieving bi-directional delivery through the nasal cavities as disclosed in WO-A-00/51672. In alternative embodiments the delivery device could be configured to deliver substance at a reduced pressure which is not sufficient to achieve bi-directional delivery through the nasal cavities. Such embodiments are still advantageous as compared to known delivery devices in providing for velum closure and being capable of achieving targeted delivery, particularly when certain regions of the nasal cavity are obstructed by cuff members.

Also, in another modification, the delivery devices could include two nosepieces, in one embodiment configured for the simultaneous delivery to each of the nasal cavities. Such embodiments would advantageously provide for three-point fixation of the delivery devices via the nosepieces and the mouthpieces.

The invention claimed is:

1. A nasal delivery device for delivering a substance to a nasal airway of a subject, comprising:
a nosepiece adapted for fitting to a nasal cavity of a subject, the nosepiece including a first delivery outlet comprising a nozzle from which a liquid spray of the substance is delivered to the nasal airway of the subject, and a second delivery outlet through which a flow of gas, separate from an exhalation breath of the subject, is delivered to the nasal airway of the subject, wherein the second delivery outlet is separate from the nozzle, and the nozzle and the second delivery outlet are disposed such that the flow of gas that is delivered through the second delivery outlet first interacts with the liquid spray as delivered from the nozzle downstream of the nozzle;

a delivery unit for delivering the substance through the first delivery outlet of the nozzle;

a gas supply unit for supplying the flow of gas through the second delivery outlet;

a mouthpiece unit through which the subject in use exhales to cause closure of an oropharyngeal velum of the subject; and an actuation mechanism for actuating the delivery unit and the gas supply unit on exhalation by the subject.

2. The delivery device of claim 1, wherein:

the gas supply unit comprises a gas pump unit for delivering the flow of gas, the gas pump unit including a first chamber containing a gas and a first piston member which is movable in the first chamber to deliver the flow of gas from the first chamber through the second delivery outlet;

the delivery unit includes a pump unit for delivering the substance to the nozzle, the pump unit including a second chamber containing the substance and a second piston member which is movable in the second chamber to deliver the substance from the second chamber through the nozzle; and the gas supply unit and the delivery unit are formed as an integrated unit and are actuatable by a driving unit for driving the first and second piston members to deliver the flow of gas through the second delivery outlet and the substance through the nozzle.

3. The delivery device of claim 2, wherein the first piston member is configured to drive the second piston member.

4. The delivery device of claim 3, wherein the driving unit is configured first to drive the first piston member alone and subsequently drive the first and second piston members in unison.

5. The delivery device of claim 2, wherein the driving unit is configured to drive the first and second piston members in a single action.

6. The delivery device of claim 5, wherein the first and second piston members are integrally formed.

7. The delivery device of claim 1, wherein the second delivery outlet provides a substantially annular outlet.

8. The delivery device of claim 7, wherein the second delivery outlet is disposed about the nozzle.

9. The delivery device of claim 1, wherein more than 50% of the particles of the liquid spray have a diameter in the range of from about 1 μm to about 80 μm.

10. The delivery device of claim 9, wherein more than 50% of the particles of the liquid spray have a diameter in the range of from about 10 μm to about 30 μm.

11. The delivery device of claim 1, wherein the flow of gas delivered from the second delivery outlet guides the liquid spray that is delivered from the nozzle.

12. The delivery device of claim 1, wherein the gas supply unit comprises a gas pump unit for delivering the flow of gas, the gas pump unit including a first chamber containing a gas and a first piston member which is movable in the first chamber to deliver the flow of gas from the first chamber through the second delivery outlet.

13. The delivery device of claim 1, wherein the delivery unit includes a pump unit for delivering the substance to the nozzle, the pump unit including a second chamber containing the substance and a second piston member which is movable in the second chamber to deliver the substance from the second chamber through the nozzle.

14. The delivery device of claim 1, wherein the actuation mechanism is configured to initiate actuation of the gas supply unit prior to actuation of the delivery unit, whereby the flow of gas is delivered through the second delivery outlet prior to delivery of the liquid spray from the nozzle.

\* \* \* \* \*

UNITED STATES PATENT AND TRADEMARK OFFICE
CERTIFICATE OF CORRECTION

PATENT NO.        : 9,205,208 B2
APPLICATION NO.   : 13/180492
DATED             : December 8, 2015
INVENTOR(S)       : Per Gisle Djupesland et al.

Page 1 of 1

It is certified that error appears in the above-identified patent and that said Letters Patent is hereby corrected as shown below:

Claims

Column 25, line 15, claim 2, "outlet:" should read as --outlet;--.

Signed and Sealed this
Fifth Day of July, 2016

Michelle K. Lee
*Director of the United States Patent and Trademark Office*